United States Patent
Hochschuler et al.

[19]

[11] Patent Number: 6,099,527

[45] Date of Patent: Aug. 8, 2000

[54] BONE PROTECTOR AND METHOD

[75] Inventors: Stephen H. Hochschuler, Plano; Robert J. Jones, Austin, both of Tex.

[73] Assignee: Spinal Concepts, Inc., Austin, Tex.

[21] Appl. No.: 09/070,323

[22] Filed: Apr. 30, 1998

[51] Int. Cl.[7] .................................................. A61B 17/56
[52] U.S. Cl. .................................. 606/61; 606/72; 606/69
[58] Field of Search .............................. 676/61, 69, 70, 676/71, 72, 79

[56] References Cited

U.S. PATENT DOCUMENTS

| | | |
|---|---|---|
| 3,644,966 | 2/1972 | Higgins . |
| 4,641,636 | 2/1987 | Cotrel . |
| 4,761,860 | 8/1988 | Krauss . |
| 4,763,644 | 8/1988 | Webb . |
| 4,790,303 | 12/1988 | Steffee .......................................... 606/72 |
| 4,966,600 | 10/1990 | Songer et al. . |
| 5,069,586 | 12/1991 | Casey . |
| 5,116,340 | 5/1992 | Songer . |
| 5,190,545 | 3/1993 | Corsi et al. .................................. 606/72 |
| 5,312,410 | 5/1994 | Miller et al. . |
| 5,318,566 | 6/1994 | Miller . |
| 5,395,374 | 3/1995 | Miller et al. . |
| 5,415,658 | 5/1995 | Kilpela et al. . |
| 5,417,690 | 5/1995 | Sennett et al. . |
| 5,423,820 | 6/1995 | Miller et al. . |
| 5,536,270 | 7/1996 | Songer et al. . |
| 5,569,253 | 10/1996 | Farris et al. . |
| 5,607,430 | 3/1997 | Bailey . |
| 5,611,801 | 3/1997 | Songer . |
| 5,626,579 | 5/1997 | Muschler et al. . |
| 5,628,756 | 5/1997 | Barker, Jr. et al. . |
| 5,649,927 | 7/1997 | Kilpela et al. . |
| 5,665,088 | 9/1997 | Gil et al. . |
| 5,665,089 | 9/1997 | Dall et al. .................................... 606/70 |
| 5,690,842 | 11/1997 | Panchison . |
| 5,693,046 | 12/1997 | Songer et al. . |
| 5,702,395 | 12/1997 | Hopf . |
| 5,702,399 | 12/1997 | Kilpela et al. . |
| 5,810,824 | 9/1998 | Chan ............................................ 606/70 |
| 5,885,294 | 3/1999 | Pedlick et al. ............................. 606/72 |
| 5,908,421 | 6/1999 | Beger ........................................... 606/74 |
| 5,919,194 | 7/1999 | Anderson .................................... 606/72 |

FOREIGN PATENT DOCUMENTS

| | | |
|---|---|---|
| 0019062 | 11/1980 | European Pat. Off. . |
| 0597258 | 5/1994 | European Pat. Off. . |
| 0625336 | 11/1994 | European Pat. Off. . |
| 0638292 | 2/1995 | European Pat. Off. . |

*Primary Examiner*—Michael Buiz
*Assistant Examiner*—Duphna Shai
*Attorney, Agent, or Firm*—Conley, Rose & Tayon, P.C.

[57] ABSTRACT

A surgical cable system and method for securing surgical cable around a portion of a human element (e.g., bone) are described. The surgical cable system may include an eyelet. The eyelet may be configured to be positionable within a cable opening formed in a portion of the bone, such that the cable may pass through the eyelet when the cable is inserted into the cable opening. The eyelet may prevent the cable from contacting the bone portion proximate the cable opening, thus protecting the bone portion from damage due to, e.g., friction from motion of the cable against the bone portion. In an embodiment, the eyelet includes a single eyelet member. In an alternative embodiment, the eyelet includes an eyelet member and at least one endpiece connectable to the eyelet member. In an alternative embodiment, the eyelet includes two eyelet members. The two eyelet members may be configurable to form a fixable engagement.

48 Claims, 18 Drawing Sheets

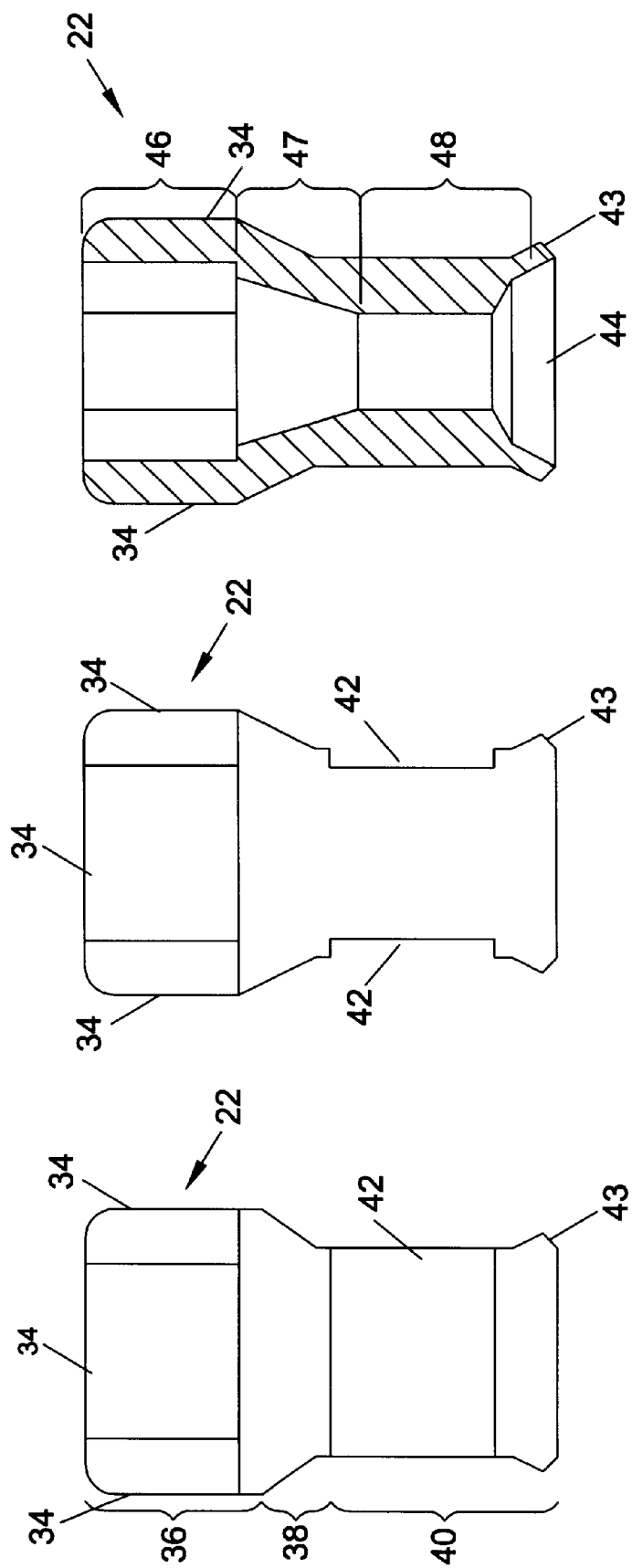

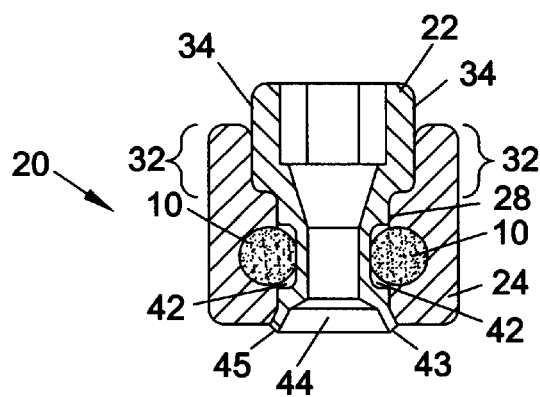
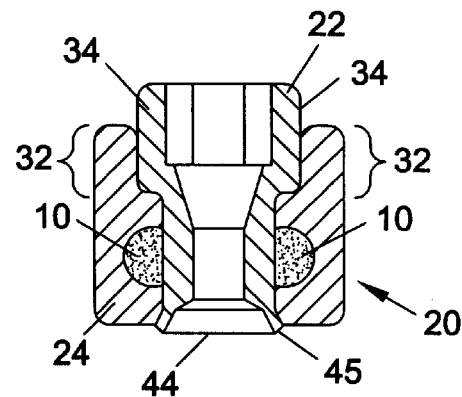
FIG. 10          FIG. 11
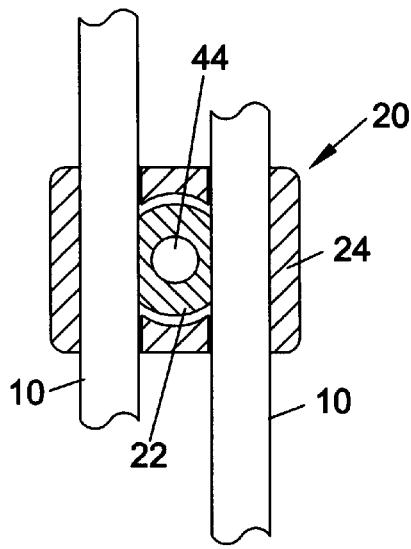
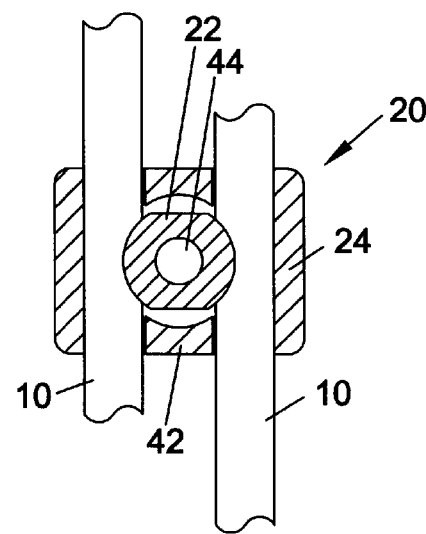
FIG. 12          FIG. 13

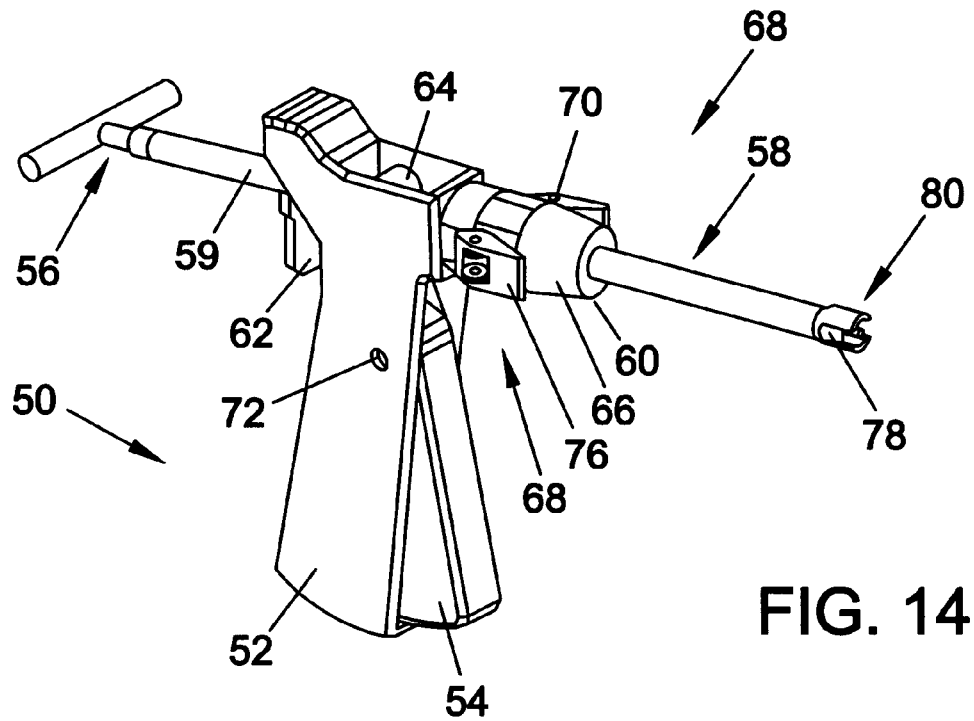
FIG. 14
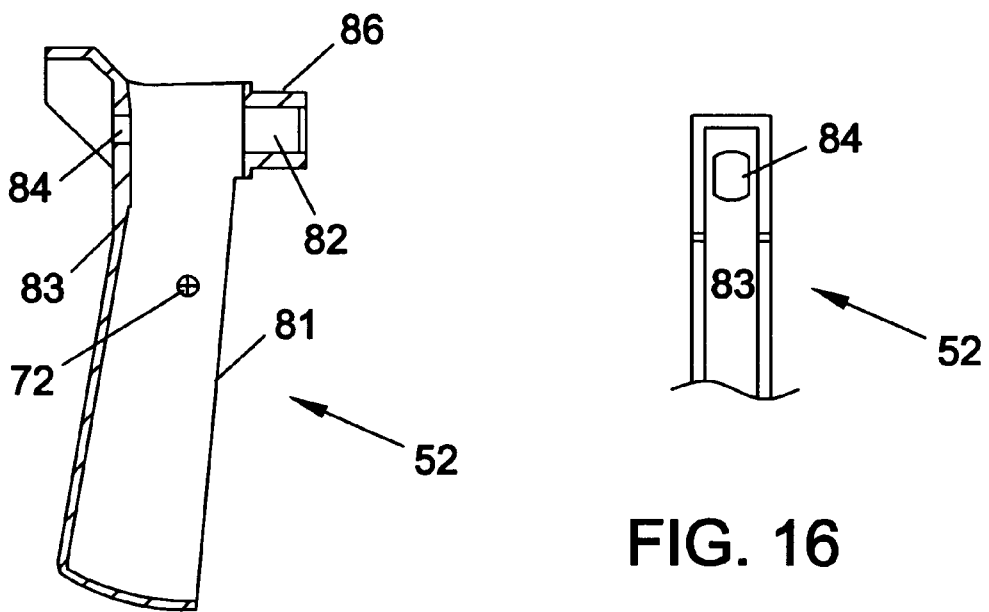
FIG. 15
FIG. 16

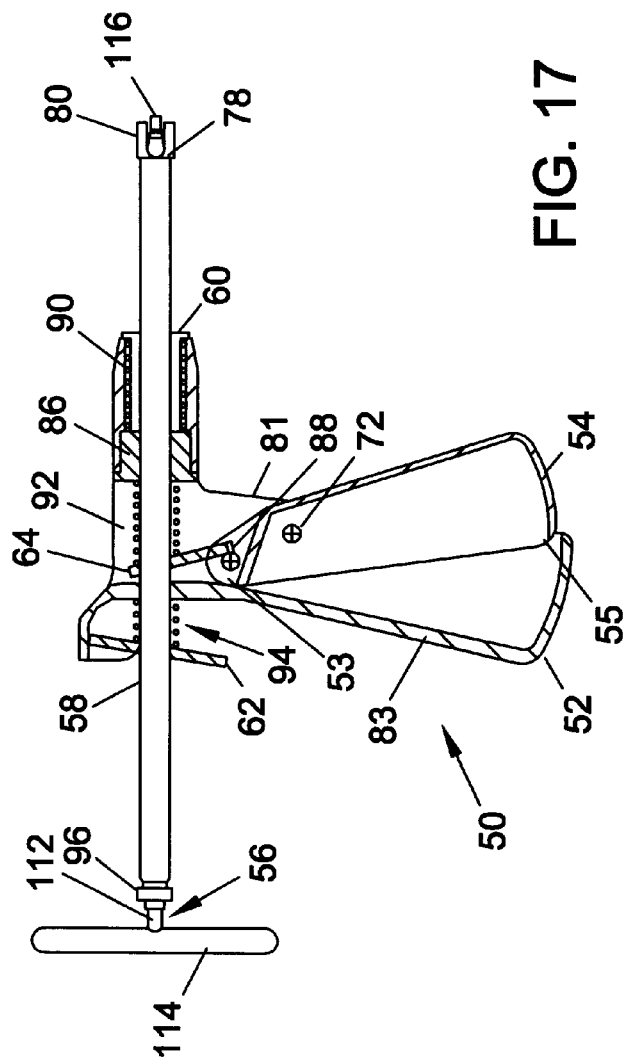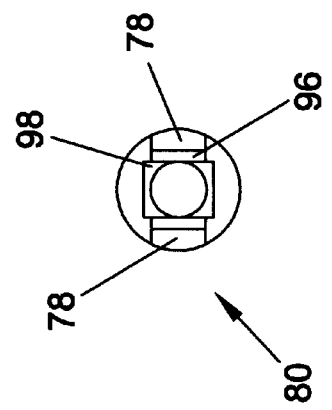

BONE PROTECTOR AND METHOD

BACKGROUND OF THE INVENTION

1. Field of the Invention

The present invention generally relates to spinal fixation systems and the like. More particularly, an embodiment of the invention relates to a spinal implant system for correction, fixation, and stabilization of the human spine to allow the development of a solid spinal fusion.

2. Description of the Related Art

Surgical cables are used in a variety of surgical procedures, including spine surgery; total hip arthroplasty; fracture fixation; closure of the sternum following open heart surgery; and oral/facial surgery to repair mandibular fractures. In these and other surgical procedures the cable may be used to set and secure bone portions in the proper orientation during the healing process.

Fractures of the vertebrae in the spinal column are very difficult to immobilize, often requiring the use of internal pins, cables and/or rods. One frequently used procedure involves wiring the fractured vertebra to one or more adjacent vertebrae to secure the vertebra in an ideal position for healing. Another method involves wiring the fractured vertebra to a rod that is similarly joined to other vertebrae. Both of these methods, as well as other techniques for spinal repair, rely on the use of cables which are secured around a portion of a vertebra.

A number of methods for encircling bone portions with surgical cables have been developed. Most of these techniques involve passing a cable around a portion of the bone and securing the cable in position using a crimp. Example of cabling apparatus and methods are illustrated in U.S. Pat. Nos. 4,966,600; 5,395,374; 5,415,658; 5,423,820; and 5,569,253. Each of these patents is incorporated by reference as if fully set forth herein. Techniques involving passing a cable through holes formed in portions of a bone are illustrated in Dickman, C. A. and Sonntag, V. K. H. [*BNI Quarterly* 9(4):2–16, 1993].

Securing a cable around and/or through a portion of a bone may cause several potential problems. To achieve a fusion between bones, the cabling system is often placed under tension. Over time, the tension on the cabling system may be decreased, due to, for example, stretching of the cable or slippage of the cable in the crimp. As a result, the cable may rub against and wear away the bone portion, allowing the cable to further slacken and negating the advantage of using the cable system. It is possible as well that motion of a cable against a bone weakened by a degenerative disease (such as osteoporosis, a frequent root cause of bone fractures) could cause the cable to wear entirely through the bone. Motion of a cable against a bone could also lead to necrosis of the bone in areas in which the cable contacts the bone. Further, a cable may fray and eventually break (due, for example, to weakness, stretching, or friction against a bone). In addition to the loss of tension in the cable assembly, fraying or breakage of the cable may produce sharp ends and cable fragments that may damage organs, nerves, and blood vessels. In order to avoid these potential problems, it would be desirable to prevent surgical cable used to stabilize a bone fracture from coming into contact with the bone.

SUMMARY OF THE INVENTION

An embodiment described herein relates to a surgical cable system that preferably includes a connector adapted to hold a cable in a loop around a human bone element and a tensioner. The connector may include a connector body, a cable, and a pin. The term "pin" within the context of this application is taken to mean any member for securing the cable within the connector body.

The connector body preferably includes a first arm and a second arm, an internal cavity, and at least two ducts. The first and second arms preferably extend from the same face of the connector body such that the connector body is substantially U-shaped. The internal cavity preferably runs longitudinally through the entire connector body and passes in between the two arms. The ducts preferably run transversally through the entire connector body, perpendicular to the internal cavity. The ducts are preferably oriented such that the ends of a cable, when the cable is passed through the ducts to form a loop, may be oriented in a substantially parallel orientation with respect to each other. The ducts are preferably located proximate to the internal cavity. The connector body preferably contains two apertures that connect two separate ducts to the internal cavity. The ducts, the apertures, and the internal cavity are oriented with respect to one another such that a cable passing through the duct may extend through the aperture into the internal cavity.

The cable is preferably substantially flexible such that the cable may form a loop for engaging a portion of a human bone. The cable is preferably of a diameter such that the cable may pass freely through a duct. The cable is also preferably of a diameter such that it may extend from the duct, through the aperture, and into the internal cavity. The cable preferably includes a tip which may inhibit the end of the cable from passing through the duct.

The pin comprises an upper portion and a lower portion. The upper portion may have a diameter that is substantially larger than the diameter of the internal cavity such that the upper portion of the pin is inhibited from passing through the internal cavity. The lower portion of the pin may have a diameter that is substantially less than the diameter of the internal cavity such that the lower portion of the pin fits within the internal cavity.

Preferably, the pin is placed within the internal cavity of the connector body before the cable is threaded. The pin may be secured within the internal cavity by deforming the bottom edge of the pin. Removal of the pin may be inhibited by the deformed bottom edge. The pin may be substantially rotatable while positioned within the internal cavity. The upper portion of the pin may contain at least two flat edges, the edges being oriented on opposing sides of the upper portion of the pin. The distance between the two edges may be less than the distance between the two arms extending from the connector body. The arms may interact with the edges such that rotation of the pin is hindered. The pin may be rotatable when sufficient force is applied to overcome the hindering force of the arms.

The pin preferably includes two grooves. The grooves may be aligned with the apertures, when the pin is inserted within the internal cavity, such that the cable may pass freely through the connector body. The pin may also be rotated, while the pin is inserted within the internal cavity, such that the grooves are perpendicular to the apertures. The rotation of the pin, after a cable has been threaded through the connector body, may exert a compressive force against the cable to secure it within the connector body. The pin may be subsequently rotated to allow free movement of the cable through the connector body.

The pin may further include an opening extending longitudinally through the entire pin. The opening preferably includes a top section and a bottom section. The top section preferably has a diameter that is substantially greater than the diameter of the end of the cable. The lower section preferably has a diameter that is substantially less than the diameter of the tip of the cable. The cable may be passed through the opening, with the tip of the cable positioned within the opening, and further through a duct to form a loop. The pin may be positioned within the internal cavity to secure the cable in place, while the cable is passed through the opening and the duct. When secured in this position the cable may be oriented in a substantially perpendicular orientation.

The cable may be passed through the ducts of the connector body such that the ends of the cable are oriented in a substantially parallel orientation. Alternatively the cable may be passed through the opening of the pin and through a duct to form a loop, the ends of the cable being in a substantially perpendicular orientation.

The surgical cable system may also include a tensioner adapted to vary the tension of the cable and secure the cable. The tensioner preferably includes a body, a shaft for contacting the connector, a driver for positioning the pin within the connector body, and an arm for adjusting the shaft.

The shaft is preferably mounted within the body, such that it extends from both sides of the body. The arm and the shaft are preferably connected such that the arm is capable of being adjusted to retract or extend the shaft from an end of the body. The body may include a stopper which secures the position of the shaft with respect to the body.

The shaft preferably includes a tip adapted to hold the connector. The tip may include a recessed opening which is shaped to couple to the connector. The shaft may also include an opening extending longitudinally through the shaft. The opening of the shaft is preferably adapted to allow the driver to pass through the shaft and onto the connector.

The body may include a cable clamp adapted to secure the cable against a portion of the body. The body preferably includes at least two cable clamps. The cable clamps may secure the cable against a portion of the body after the cable is threaded through the connector and around a portion of a human bone. The shaft may engage the connector, after the cable has been secured with respect to the body, such that movement of the shaft causes the tension of the cable to vary.

The driver may include an end adapted to engage the pin of the connector. The driver preferably includes a handle to allow the driver to be moved in a circular motion. The shaft preferably includes an opening, extending longitudinally through the shaft, that allows the driver to engage the pin while the connector is in contact with the shaft. The driver may engage the pin such that rotation of the driver causes the pin to rotate into a position which secures the cable within the connector. While the cable is secured the cable is no longer able to move within the connector. Subsequent to securing the cable, the driver may be rotated to cause the pin to move into a position which allows the cable to once again have mobility within the connector.

An embodiment of the invention relates to a surgical implant system having an eyelet used to protect bone from damage when a surgical cable is passed around a portion of the bone. In the context of this application, an "eyelet" is an element that is adapted to receive a cable during use. In the context of this application a cable "passed around" a portion of a bone includes both a cable looped around an exterior surface of the bone portion and a cable inserted into a hole formed in the bone portion. The implant system may include an eyelet member or members placed in contact with the portion of the bone, as well as a cable running through the eyelet member or members.

In an embodiment, the eyelet includes a substantially elongated eyelet member. The eyelet member may be made of titanium, stainless steel, ceramic, plastic, polymer, composite material, or other biocompatible material. For purposes of this description, "biocompatible material" is material not rejected by the body and/or not causing infection following implantation. The eyelet member preferably encloses a bore extending longitudinally through the eyelet member and having openings at a first end and at a second end. The eyelet member and bore so enclosed may be substantially cylindrical in shape. Alternatively, the eyelet member and bore may be other than circular (e.g., substantially square, rectangular, hexagonal, or ellipsoid) in cross-section. The eyelet member and the bore may be of substantially the same cross-sectional shape; alternatively, the eyelet member and the bore may be of substantially different shapes in cross-section. The bore may be completely enclosed by sides of the eyelet member. Alternatively, the eyelet member may be configured such that sides of the eyelet member only partially enclose the bore. An outer surface of the eyelet member may include protrusions extending from the outer surface of the eyelet member to form an engagement with the bone. The protrusions may serve to inhibit motion of the eyelet member with respect to the bone.

A cable opening may be formed in a portion of a bone and a surgical cable inserted into the cable opening for setting and/or securing the bone portion as a part of surgery. Preferably, the eyelet member is inserted into the cable opening and the cable is inserted into the eyelet member such that the cable does not contact the bone portion adjacent the cable opening during use. The eyelet member may be of sufficient length that at least one end of the eyelet member includes a portion extending out of the cable opening. The at least one end of the eyelet member may be deformable. After insertion of the eyelet member into the cable opening, the deformable end may be deformed such that the deformed end has a width greater than a width of the cable opening. The deformed end of the eyelet member may thus be prevented from re-entering the cable opening. The deformed end may enclose a bore such that the cable may pass through the bore in the deformed end.

Alternatively, the eyelet may include at least one endpiece configured to form a fixable engagement with an end of the eyelet member. The endpiece may be of a width greater than a width of the eyelet member such that the endpiece prevents the end of the eyelet member with which it is engaged from passing through the cable opening. In an embodiment, the endpiece may enclose a bore having a width substantially similar to a width of the eyelet member. An inner surface of the endpiece bore may include threading complementary to threading included on an outer surface of the eyelet member. Following insertion of the eyelet member into the cable opening, the endpiece may be screwed onto the eyelet member to form the fixable engagement. The endpiece may include an outer surface having protrusions extending therefrom. The protrusions may extend into the bone to substantially inhibit motion of the eyelet with respect to the bone during use.

Alternatively, an outer surface of the eyelet member may include at least one groove, and an inner surface of the endpiece bore may include at least one projection. The endcap may be snapped onto the eyelet member such that the groove and the projection may form a fixable engagement between the endpiece and the eyelet member. Alternatively, the outer surface of the eyelet member may include at least one projection and the endpiece may include at least one groove for forming a fixable engagement as described above. The endpiece may include an outer surface having protrusions extending therefrom. The protrusions may extend into the bone to substantially inhibit motion of the eyelet with respect to the bone during use. The endpiece may include an elongated opening formed in a side of the endpiece to permit alteration of the width of the endpiece during formation of the fixable engagement.

Alternatively, the eyelet may include both an eyelet member with a deformable first end and an endpiece configured to form a fixable engagement with the eyelet member at a second end opposite the first end. Deformation of the first end and formation of the fixable engagement may be as described previously. The deformed first end and the endpiece may prevent the ends of the eyelet member from entering the cable opening and thus cause the eyelet to remain in contact with the bone. The endpiece may include an exterior surface having protrusions extending therefrom for substantially inhibiting motion of the eyelet with respect to the bone.

In an alternative embodiment, the eyelet may include (a) an eyelet member having a substantially elongated first portion located at a first end of the eyelet member and having a first width, and (b) a second portion located at a second end of the eyelet member and having a width substantially greater than the first width. The eyelet member may be made of titanium, stainless steel, ceramic, plastic, polymer, composite material, or other biocompatible material. The eyelet member preferably includes a bore extending longitudinally through the eyelet member and having openings at each end. The eyelet member and bore may be substantially cylindrical in shape. Alternatively, the eyelet member and bore may be other than circular (e.g., square, rectangular, hexagonal, ellipsoid) in cross-section. The bore may be completely enclosed by sides of the eyelet member. Alternatively, the eyelet member may be configured such that sides of the eyelet member only partially enclose the bore.

A cable opening may be formed in a portion of a bone and a surgical cable inserted into the cable opening for setting and/or securing the bone portion as a part of surgery. Preferably, the eyelet member is inserted into the cable opening and the cable is inserted into the eyelet member such that the cable does not contact the bone portion during use. The second portion of the eyelet member may be of sufficient width to prevent the eyelet member from passing completely through the cable opening.

The eyelet member may be of sufficient length such that the first portion of the eyelet member extends out of the cable opening. The first end of the eyelet member may be deformable. After insertion of the eyelet member into the cable opening, the first end extending out of the cable opening may be deformed such that the deformed end has a width greater than a width of the cable opening. The deformed end of the eyelet member may thus be prevented from re-entering the cable opening. The deformed end may enclose a bore such that the cable may pass through the bore in the deformed end.

Alternatively, the eyelet may include an endpiece configured to form a fixable engagement with the first end of the eyelet member. The endpiece may be of a width greater than a width of the eyelet member such that the endpiece prevents the first end of the eyelet member with which it is engaged from passing back through the cable opening. In an embodiment, the endpiece may enclose a bore having a width substantially similar to a width of the eyelet member. An inner surface of the endpiece bore may include threading complementary to threading included on an outer surface of the eyelet member. Following insertion of the eyelet member into the cable opening, the endpiece may be screwed onto the eyelet member to form the fixable engagement. The endpiece may include an outer surface having protrusions extending therefrom. The protrusions may extend into the bone to substantially inhibit motion of the eyelet with respect to the bone during use.

Alternatively, an outer surface of the eyelet member may include at least one groove, and an inner surface of the endpiece bore may include at least one projection. The endcap may be snapped onto the eyelet member such that the groove and the projection may form a fixable engagement between the endpiece and the eyelet member. Alternatively, the outer surface of the eyelet member may include at least one projection and the endpiece may include at least one groove for forming a fixable engagement as described above. The endpiece may include an exterior surface having protrusions extending therefrom for substantially inhibiting motion of the eyelet with respect to the bone during use.

In an alternative embodiment, the eyelet includes a first and a second eyelet member of substantially similar cross-section. Each eyelet member may include a bore having openings at opposite ends of the eyelet member. The eyelet members and bores may be substantially cylindrical in shape. Alternatively, the eyelet members and bores may be other than circular (e.g., square, rectangular, hexagonal, ellipsoid) in cross-section. The bore may be completely enclosed by sides of the eyelet member. Alternatively, the eyelet members may be configured such that sides of the eyelet members only partially enclose the bore.

At least one of the eyelet members may include a substantially elongated first portion at a first end and a second portion at a second end; the second portion may have a width greater than a width of the first portion. The eyelet member may be made of titanium, surgical steel, ceramic, plastic, polymer, composite material, or other biocompatible material. The eyelet member preferably includes a bore extending longitudinally through the eyelet member and having openings at each end. The eyelet member and bore may be substantially cylindrical in shape. Alternatively, the eyelet member and bore may be other than circular (e.g., square, rectangular, hexagonal, ellipsoid) in cross-section. The bore may be completely enclosed by sides of the eyelet member. Alternatively, the eyelet member may be configured such that sides of the eyelet member only partially enclose the bore.

A cable opening may be formed in a portion of a bone and a surgical cable inserted into the cable opening for setting and/or securing the bone portion as a part of surgery. Preferably, the eyelet member is inserted into the cable opening and the cable is inserted into the eyelet member such that the cable does not contact the bone portion during use. The second portion of the eyelet member may be of sufficient width to prevent the eyelet member from passing completely through the cable opening.

A lateral wall of an eyelet member may be rounded, tapered, beveled, or otherwise shaped at an end of the eyelet member such that the diameter of the bore is gradually increased at the end. This shaping may serve to smooth the end of the bore and prevent wear on the cable where the cable passes into and out of the eyelet member.

The eyelet members may be of substantially uniform size and shape such that they partially or completely fill the hole in the bone upon insertion, without engaging each other. Alternatively, the outer diameter of one eyelet member may be smaller than the inner diameter of the other eyelet member such that one eyelet member may be partially or completely inserted within the other. Alternatively, the inner surface of one eyelet member may have one or more grooves formed therein. The outer surface of the other eyelet member may have ridges extending from it. The ridges may be of a size and shape such that they fit into the grooves on the first eyelet member. When the second eyelet member is inserted into the first eyelet member, the ridges may engage the grooves and form an interlock, such that the eyelet members may be fixed in the hole in the bone and not likely to slide out. In still another embodiment, the inner surface of one eyelet member and the outer surface of the other may be compatibly threaded such that the eyelet members may be screwed together and thus more firmly fixed within the hole.

An advantage of the present invention is that damage to the bone may be prevented.

BRIEF DESCRIPTION OF THE DRAWINGS

Further advantages of the present invention will become apparent to those skilled in the art with the benefit of the following detailed description of the preferred embodiments and upon reference to the accompanying drawings in which:

FIG. 4 depicts a cross sectional view of a pin as viewed facing a groove from the front face;

FIG. 5 depicts a side view of the pin;

FIG. 6 depicts a cross sectional view of the pin as viewed from the front;

FIG. 10 depicts a cross sectional view of the connector, with the cable being movable within the connector body, as viewed from the side;

FIG. 11 depicts a cross sectional view of the connector, with the cable being secured in an immobile position within the connector, as viewed from the side;

FIG. 12 depicts a cross sectional view of the connector, with the cable being movable within the connector body, as viewed from the bottom;

FIG. 13 depicts a cross sectional view of the connector, with the cable secured in an immobile position within the connector body, as viewed from the bottom;

FIG. 14 depicts a perspective view of a tensioner;

FIG. 15 depicts a cross sectional view of a body of the tensioner, as viewed from the side;

FIG. 16 depicts a rear view of the body of the tensioner;

FIG. 17 depicts a cross sectional view of the tensioner, as viewed from the side;

FIG. 18 depicts a tip of a shaft of the tensioner, as viewed from the front;

FIG. 19 depicts the tip of the shaft as viewed from the side;

Figure 1:
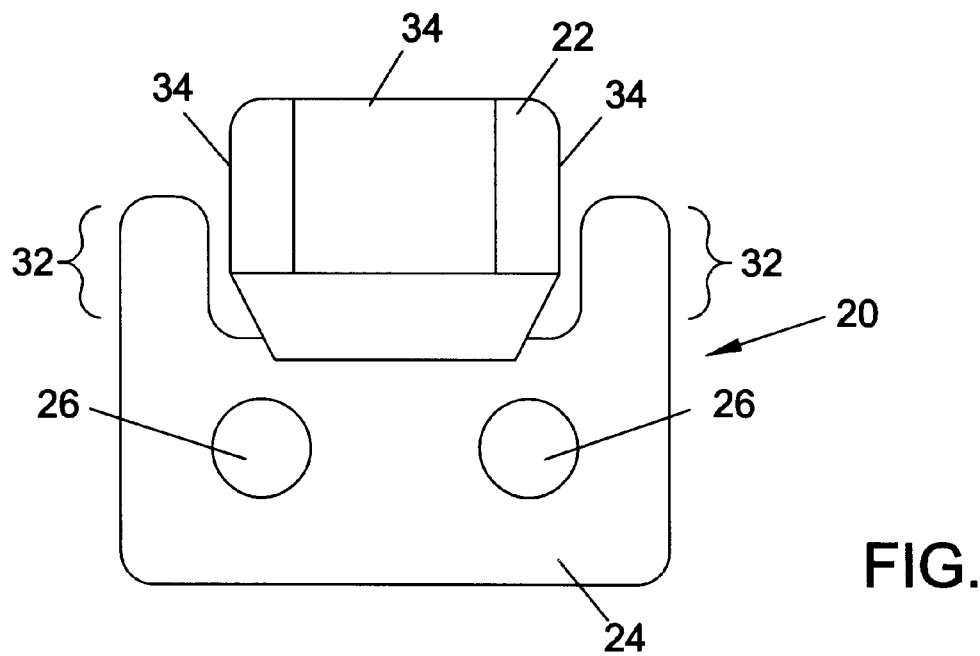
FIG. 1 depicts a side view of a connector.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

FIG. 1 depicts an embodiment of a connector 20. The connector 20 includes a connector body 24 and a pin 22. A cable 10 may be passed through the ducts 26 to form a loop for engaging a portion of a human bone. The cable 10 may be looped around a variety of human bone portions involved in various surgical procedures. The surgical procedures which may make use of a surgical cable system include, but are not limited to, spine surgery; total hip arthroplasty; fracture fixation; closure of the sternum following open heart surgery; and oral/facial surgery to repair mandibular fractures. The cable 10 is preferably used for engaging a portion of the human spine.

Figure 2:
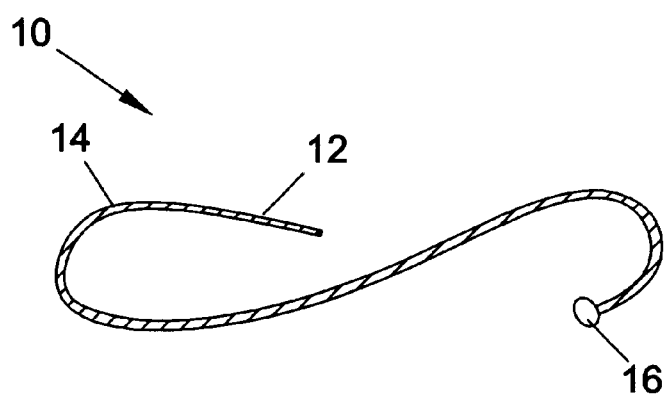
FIG. 2 depicts a perspective view of a cable.

The term "cable" within the context of this application means any elongated flexible member, including single strand elements (e.g., stainless steel wires, monofilament lines, etc.) and multi strand elements (cords, threads, twisted wires bundled together, etc.). An embodiment of a cable is illustrated in FIG. 2. The cable 10 includes a leader portion 12, a main portion 14, and a tip 16. The main portion 14 is preferably comprised of a substantially flexible stranded metal wire. The main portion 14 may be comprised of any substantially flexible material including, but not limited to, cloth, fiber, steel, nylon, monofilament, or various plastics. The main portion 14 is preferably made of titanium or stainless steel. Alternately, the main portion 14 of the "cable" may simply be thread, line, or string.

The cable 10 preferably has a leader portion 12 attached to an end of the cable. The leader portion 12 may include a non-stranded wire that is substantially less flexible than the main portion 14. The leader portion 12 may include any substantially flexible material including, but not limited to, cloth, fiber, monofilament, steel, nylon, or various plastics. The leader portion 12 is preferably made of titanium or stainless steel. The leader portion 12 is preferably made of the same material as the main portion 14 of the cable 10. The leader portion 12 may be used to guide the cable 10 around the bone and through the various openings of the connector 20.

The cable 10 may include a tip 16 attached to an end of the cable. The tip 16 is preferably of a diameter that is substantially larger than the diameter of the main portion 14. The tip 16 may be made of the same material as the main portion. The tip 16 is preferably made of titanium or stainless steel. The tip 16 may be larger than the diameter of the ducts 26, (shown in FIG. 1), such that the tip 16 is inhibited from passing through the ducts. Thus, tip 16 may function to prevent the cable 10 from passing entirely through the ducts 26.

The cable 10 is, in one embodiment, made by twisting together multiple wire strands around a cable core. The wire strands are preferably made by twisting six filaments around a central filament in a helical orientation. The filaments may be made by reducing the diameter of a wire to a thickness of less than 0.005 inch, and more preferably to a diameter of 0.003 inch. The cable core may be made by twisting six wire strands over a central strand in a helical orientation. The cable 10 may be made by twisting twelve strands over the cable core. After the strands are twisted to form the cable 10, the cable may be hammered repeatedly to give a smooth surface. The cable 10 may be cut into the appropriate length by a cutting apparatus. The cable 10 is preferably cut by a laser. By applying tension on the cable 10 during the cutting process an end of the cable may be formed into an enlarged tip 16. The leader portion 12 may be welded onto an end of the cable 10 before use. The cable may be cleaned repeatedly during the manufacturing procedure.

Figure 3:
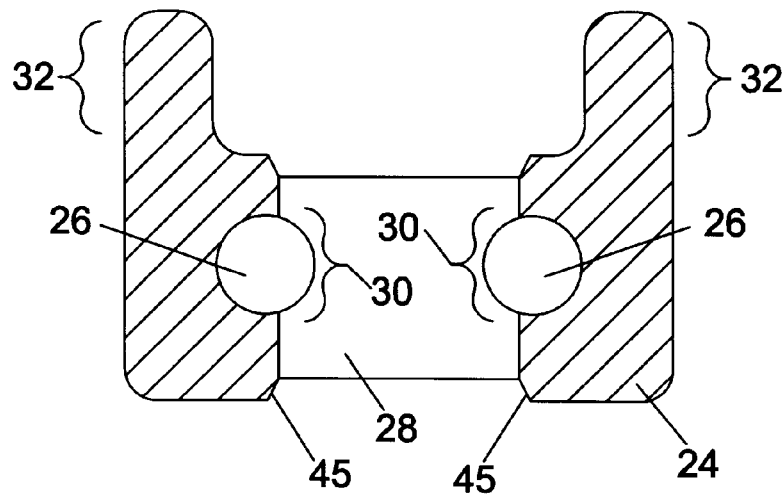
FIG. 3 depicts a cross sectional view of the connector as viewed from the side.

FIG. 3 depicts a cross-sectional view of the connector body 24 of the connector 20. The connector body 24 preferably includes an internal cavity 28 for holding a pin 22 within the connector body 24. The internal cavity 28 may be substantially cylindrical in shape and preferably passes longitudinally through the entire connector body 24. The connector body 24 may include a duct 26 that passes transversally through the entire connector body. The duct 26 is preferably oriented substantially perpendicular to the internal cavity 28. The connector body 24 preferably includes at least two ducts 26 that pass transversally through the entire connector body. The ducts 26 preferably communicate with the internal cavity 28 via an aperture 30. The ducts 26 are preferably positioned such that a cable 10 lying within the duct may extend into the internal cavity 28.

The pin 22 preferably includes an upper portion 36 and a lower portion 40, as depicted in FIG. 4. The pin 22 may also include a transition portion 38 oriented between the upper potion 36 and the lower portion 40. The upper portion 36 is preferably of a diameter substantially larger than the diameter of the lower portion 40. The upper portion 36 is preferably of a diameter such that it is incapable of passing into the internal cavity 28. The lower portion 40 of the pin 22 is preferably of a diameter such that the lower portion may fit into the internal cavity 28 (shown in FIG. 2). The diameter of the transition portion 38 may be variable, becoming narrower in a direction from the upper portion 36 toward the lower portion 40. The bottom of the pin 43 may be deflected outward to substantially secure the pin 22 within the internal cavity 28.

Figure 9:
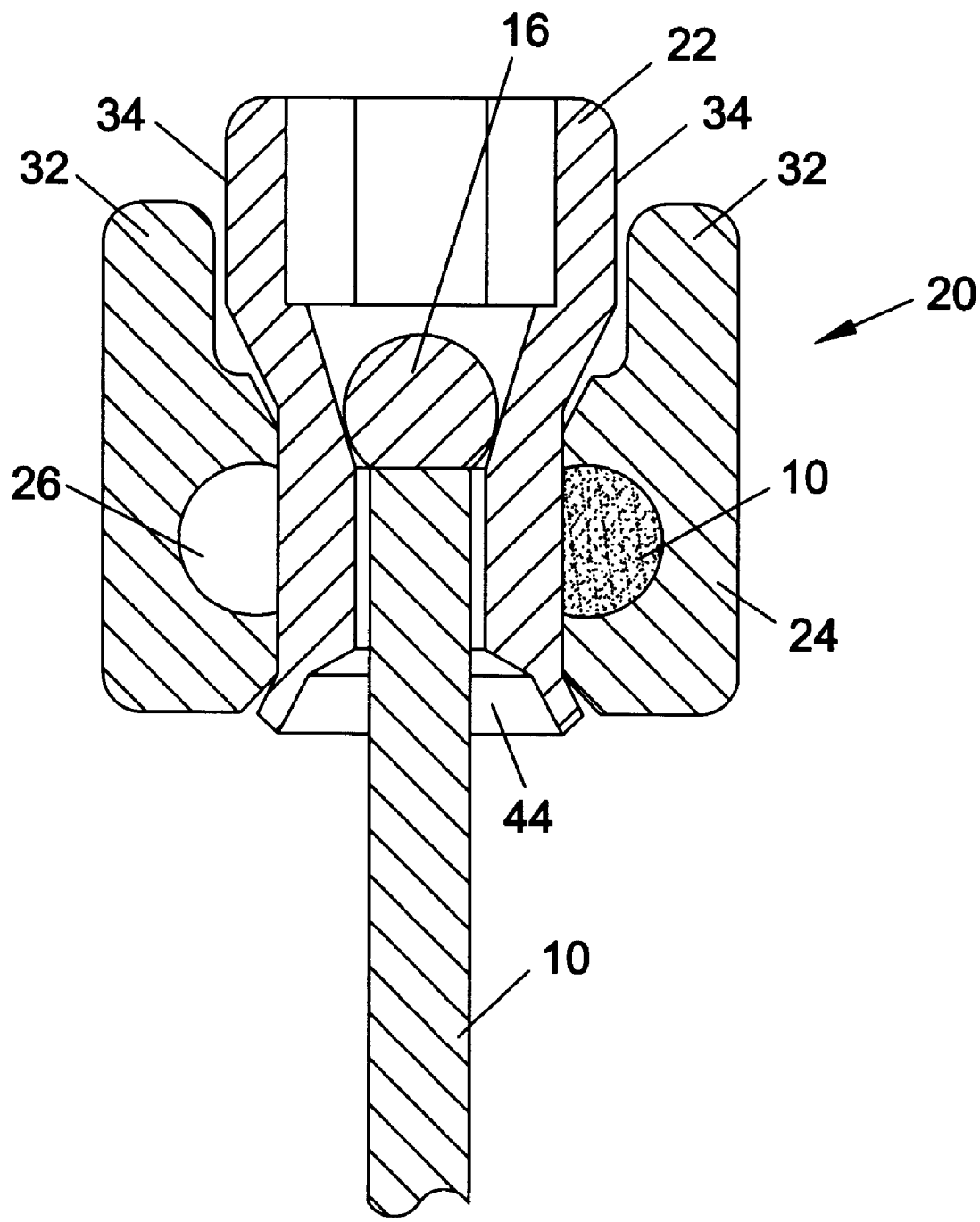
FIG. 9 depicts a cross sectional view of the connector in a secured position, with a portion of the cable residing in an opening of the pin, as viewed from the side of the connector.

In another embodiment, the pin 22 preferably includes two grooves 42, as depicted in FIG. 5. The grooves 42 may be substantially rectangular in shape, including a width that is substantially larger than the diameter of the cable 10. The grooves 42 are preferably oriented on opposing sides of the lower portion 40 of the pin 22. Referring to FIG. 9, the pin 22 may lie within the internal cavity 28 such that the grooves 42 lie in the plane defined by the ducts 26. The grooves 42 may be substantially aligned with the ducts 26, with an aperture 30 positioned between each duct and groove. The pin 22 may be oriented within the internal cavity 28, with the grooves 42 substantially aligned with the ducts 26, such that the cable 10 may pass freely through the connector body 24. The pin 22 may also be oriented within the internal cavity 28, with the grooves 42 positioned substantially perpendicular to the ducts 26, such that the cable 10 is secured within the connector body 24.

In another embodiment, the pin 22 preferably includes an opening 44, as depicted in FIG. 6. The opening 44 is preferably substantially cylindrical in shape and preferably passes longitudinally through the entire pin 22. The pin may surround a portion of the opening such that the opening is U-shaped or V-shaped. The pin preferably surrounds the entire opening. The opening 44 preferably includes an upper portion 46 and a lower portion 48. The pin 22 may also include a transition portion 47 oriented between the upper potion 46 and the lower portion 48. The upper portion 46 is preferably of a diameter substantially larger than the diameter of the lower portion 48. The diameter of the upper portion 46 is preferably substantially larger than the diameter of the tip 16 of cable 10. The diameter of the lower portion 48 is preferably substantially smaller than the diameter of the tip 16 of cable 10. In this manner, the opening 44 may prevent a cable 10, having a tip 16, from passing completely through the opening.

The upper portion 46 of the opening 44 may be chosen to couple with any suitable device adapted to apply a torsional force. The upper portion 46 may be substantially rectangular for receiving a flat-head torsioning device, such as a screwdriver. The upper portion 46 may also be substantially cross shaped for receiving a cross-shaped head of a torsioning device, such as a PHILLIPS screwdriver. The upper portion 46 is preferably hexagonal in shape for receiving a hexagonal head of a torsioning device, such as an Allen wrench.

Figure 7:
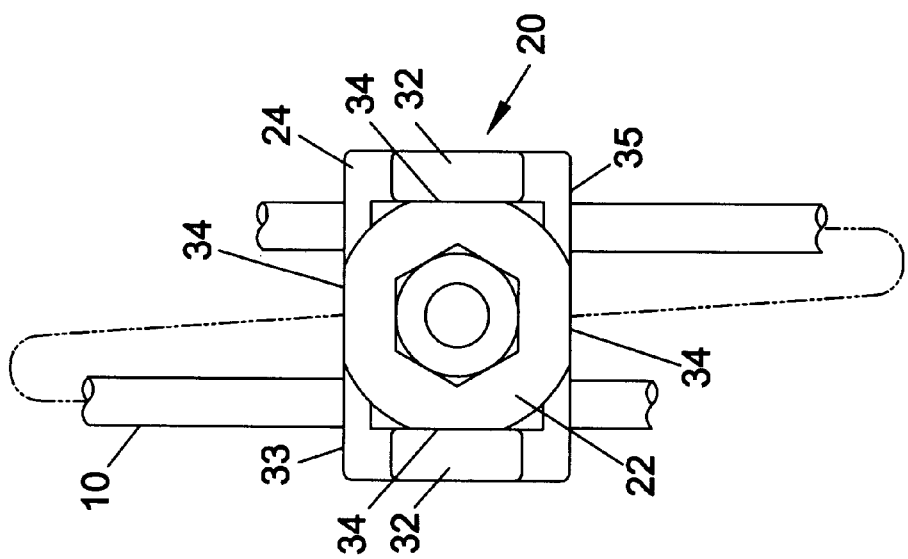
FIG. 7 depicts a top view of the connector with the cable forming a loop by entering a first face opposite to a second face from which it exits.

FIG. 7 depicts a connector 20 with a cable 10 threaded through the connector body 24 to form a loop according to one embodiment. The cable 10 is preferably threaded through a duct 26, around a human bone element, and back through a separate duct 26 to form a loop. The loop is formed such that the ends of the cable 10 lie in a substantially parallel orientation with respect to each other. The cable 10 is preferably threaded through a duct 26, around a human bone element, and back through another duct to form a loop, reentering the connector body 24 from the face 35 on the side opposite to the face 33 which the cable initially exited. The pin 22 may be inserted within the connector body 24, after the cable 10 has been looped around a human bone element and passed through the connector body 24 to secure the cable within the connector body. The pin 22 may be removed from the connector body 24, subsequent to securing the cable 10 within the connector body, to allow the cable to be moved within the connector body. Removal of the pin 22 may be prevented by deforming the bottom of the pin.

Figure 8:
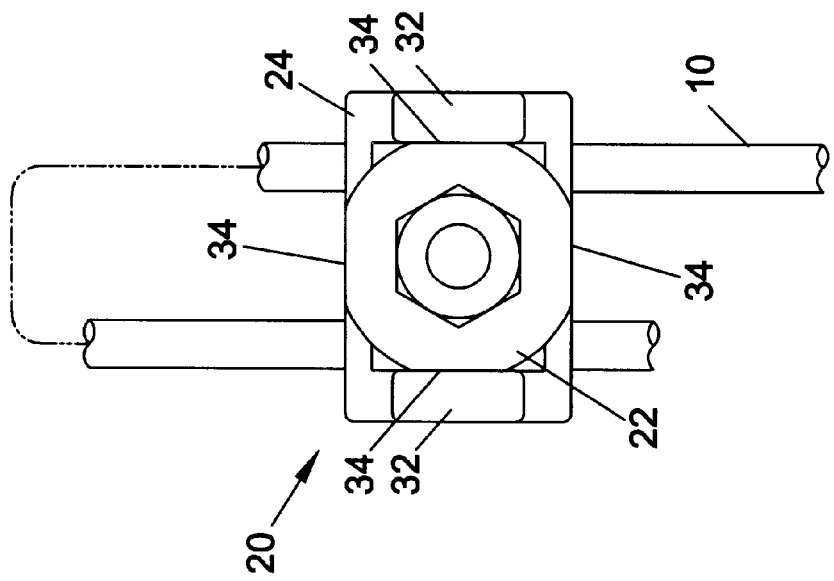
FIG. 8 depicts a top view of a connector with the cable forming a loop by entering the same face from which it exits.

FIG. 8 depicts another embodiment in which the cable 10 is preferably threaded through a duct 26, around a human bone element, and back through a separate duct to form a loop, reentering the connector body 24 from the same face 33 of the connector body that the cable initially exited. The pin 22 may be inserted within the connector body 24 to secure the cable 10 within the connector body. While the cable 10 is secured the cable is no longer able to move within the connector 20. The pin 22 may be removed from the connector body 24, subsequent to securing the cable 10 within the connector body, to allow the cable to be moved within the connector body.

FIG. 9 depicts another embodiment in which the cable 10 is preferably threaded through the opening 44, around a human bone element, and back through a duct 26 to form a loop. In this manner, the ends of the cable 10 may lie in a substantially perpendicular orientation with respect to each other (not shown). The pin 22 may be inserted within the connector body 24 to secure the cable 10 within the connector body. The pin 22 may be removed from the connector body 24, subsequent to securing the cable 10 within the connector body, to allow the cable to be movable within the connector body. Tension on the cable 10 may pull the tip 16 of the cable against the lower portion 48 of the opening 44. In this manner, the cable 10 may be prevented from moving within the opening 44.

The pin 22 may be positioned within the internal cavity 28 before the cable 10 is threaded through the ducts 26. The cable 10 may be threaded through the ducts 26 of the connector body 24 while the pin 22 is mounted within the internal cavity 28. The pin 22 is preferably oriented such that the grooves 42 of the pin are substantially aligned with the ducts 26, as depicted in FIGS. 10 and 12. The pin 22 may be rotated, subsequent to the cable 10 being passed through the connector body 24, such that the grooves 42 are substantially perpendicular to the ducts 26. As a result, the ungrooved portion of the pin 22 may compress the cable 10 against the connector body 24, securing the cable, as depicted in FIGS. 11 and 13. Subsequent to securing the cable 10 within the connector body 24, the pin 22 may be further rotated such that the grooves 42 are once again aligned with the ducts 26. In this manner, the cable 10 may be repeatedly moved and secured within the connector body 24.

In another embodiment, the cable 10 may be threaded through the pin 22 and through a duct 26 of the connector body 24, as depicted in FIG. 9. The pin 22 may be rotated within the connector body 24 to secure the cable 10 in an immobile position within the connector body. Subsequent to securing the cable 10 in an immobile position within the connector body 24, the pin 22 may be further rotated such that the cable may again be movable within the connector body. Tension on the cable 10 may pull the tip 16 of the cable against the lower portion 48 of the opening 44. In this manner, the cable 10 may be prevented from moving within the opening 44.

The connector body 24 preferably has two substantially flat arms 32 extending out from the top face of the connector body, as depicted in FIG. 9. The arms 32 are preferably oriented opposite to each other, and the internal cavity 28 is preferably located between the two arms. The upper portion 36 of the pin 22 may have at least two substantially flat edges 34. The upper portion 36 of the pin 22 more preferably has four substantially flat edges 34 (shown in FIG. 7). The edges 34 are preferably oriented on opposing sides of the upper portion 36 of the pin 22. The pin 22 may be mounted within the internal cavity 28 such that the edges 34 are contained by the arms 32 of the connector body 24. The arms 32 may interact with the edges 34 such that rotation of the pin 22 is hindered. The pin 22 may be rotatable when sufficient force is applied to the pin to overcome the hindering force of the arms 32.

As illustrated in FIG. 10 the pin 22 may be inserted within the internal cavity 28 and the pin bottom 43 deflected outward. The diameter of the bottom 45 of the internal cavity 28 is preferably tapered, becoming wider in a direction toward the bottom 45 of the connector body 24. The deflection of the bottom 43 of pin 22 is tapered to match the tapering of the internal cavity 28. The pin 22 is preferably rotatable within the internal cavity 28. The lower portion 40 of the pin 22 is preferably of a diameter such that, when positioned within the internal cavity 28, the lower portion may compress the cable 10 against the wall of the duct 26, securing the cable in place.

The cable 10 is preferably formed into a loop and tensioned prior to securing the cable within the connector body 24. When the cable 10 is under tension, the corners of the edge 34 of the pin 22 may rest upon the inner faces of the arms 32. The force exerted by the arms 32 upon the corners of the edges 34 may prevent the pin 22 from rotating due to the tension of the cable 10. The pin 22, however, may be rotated by an operator to a position which allows the cable 10 to be movable through the connector body 24. The force required by the operator to move the pin 22 into an unsecured position is preferably greater than the rotational force exerted on the pin by the cable 10 when in a secured position.

The surgical cable system preferably includes a tensioner 50 adapted to vary the tension of the cable 10 and secure the cable within the connector 20. A preferred embodiment of the tensioner 50 is depicted in FIG. 14. The tensioner 50 preferably includes a body 52, a shaft 58 for contacting the connector 20, a driver 56 for positioning the pin 22 within the connector 20, and an arm 54 for adjusting the position of the shaft 58. The parts of the tensioner 50 may be made of a variety of substantially inflexible materials including, but not limited to, instrument grade stainless steel, aluminum, and various plastics.

FIG. 15 depicts a cross sectional side view of the body 52. The body 52 is preferably substantially rectangular and hollow. The body 52 preferably includes a substantially circular front opening 82 and a substantially oval rear opening 84. The body 52 may also include a bushing holder 86 extending from the front edge 81 of the body. The front opening 82 may pass through the bushing holder 86. The front opening 82 and the rear opening 84 may be aligned such that a rigid, elongated member may be passed through both openings. The front edge 81 of the body 52 may be uncovered allowing insertion of the arm 54 within the body.

FIG. 16 depicts a preferred embodiment of the rear opening 84 of the body 52. The rear opening 84 preferably comprises two curved sections and two flat sections. The curved sections may be oriented at the top and the bottom of the rear opening 84. The flat sections may connect the top curved section to the bottom curved section to form a substantially oval opening.

The arm 54 may be substantially hollow and is preferably mounted within the hollow portion of the body 52, as depicted in FIG. 17. The arm 54 may be held in place by the arm pin 72. The arm pin 72 may be substantially cylindrical and hollow. The arm pin 72 may extend through the entire arm 54 and partially into the sides of the body 52. The arm pin 72 may be mounted within the body 52 such that the arm 54 is pivotable about the arm pin in a range of about 45 degrees. The arm 54 may be stopped in a forward position when the top 53 of the arm comes into contact with the body 52, as depicted in FIG. 17. The arm 54 may be similarly stopped in a rear position when the bottom 55 of the arm 54 comes into contact with the body 52. The sides of the arm 54 preferably extend above the top of the arm to form a substantially U-shaped pocket. The U-shaped pocket may be adapted to hold a push tab pin 88 that may be mounted over the top of the arm 54 extending into the sides of the arm.

Turning to FIG. 17, the push tab 64 may be substantially rectangular. The push tab 64 preferably includes a substantially circular aperture. The push tab 64 may rest on the front portion of the push tab pin 88. The aperture of the push tab 64 is preferably sized such that the shaft 58 may be passed through the aperture. The push tab 64 is preferably placed within the hollow portion of the body 52. The shaft 58 is preferably fitted through the aperture of the push tab 64, and the lower portion of the push tab is preferably seated against the push tab pin 88. The arm spring 92 may also lie on the shaft 58, preferably positioned between the push tab 64 and the front 81 of the body 52.

The arm 54 is preferably pivotable about the arm pin 72 such that a bottom portion 55 of the arm may be moved toward the rear 83 of the body 52. Rearward motion of the arm 54 preferably causes the push tab pin 88 to move toward the front 81 of the body 52. Push tab 64 preferably rests against the push tab pin 88. Thus, movement of the push tab 64 toward the front 81 preferably makes the push tab pin 88 move in a similar direction. As a result, the push tab 64 may engage the shaft 58, propelling the shaft through the front opening 82 of the body 52. Concurrent with the movement of the arm 54, the push tab 64 may also compress the arm spring 92. In the absence of any pressure on arm 54, the arm spring 92 preferably expands such that the push tab 64, the push tab pin 88, and the arm 54 are returned to their original positions.

The body 52 may further include a lock tab 62 and lock spring 94. The lock tab 62 may be substantially rectangular. The lock tab 62 preferably includes a substantially circular aperture. The lock tab 62 may extend downward from the top of the body 52, as depicted in FIG. 17. The aperture is preferably sized such that the shaft 58 may be passed through the aperture. The lock spring 94 may also lie on the shaft 58, preferably positioned between the lock tab 62 and the body 52. The lock spring 94 preferably exerts a force on the lock tab 62, forcing it away from the rear 83 of the body 52. Movement of the lock tab 62 in this direction is preferably restricted when the lower portion of the aperture comes into contact with the shaft 58. The force exerted by the lock tab 62 upon the shaft 58 may restrict the rearward motion of the shaft through the body 52.

The lock tab 62 may be moved toward the front 81 of the body 52 such that the aperture no longer comes into contact with the shaft 58. When oriented in this forward position the lock tab 62 may no longer restrict the rearward motion of the shaft 58. The lock tab 62 is preferably moved into the forward position to allow the shaft 58 to be moved in a rearward direction within the body 52. Movement of the lock tab 62 toward the front of the body 52 may also compress the lock spring 94. When the pressure being applied to the lock tab 62 is released, the lock spring 94 preferably pushes the lock tab 62 back into its starting position.

The shaft 58 may be a variety of shapes including, but not limited to cylindrical, oval or trapezoidal. The shaft 58 is preferably substantially cylindrical and hollow. The shaft 58 may include two flat edges 59 (shown in FIG. 14) that run longitudinally along the entire length of the shaft 58. The edges 59 are preferably oriented on opposing sides of the shaft 58, giving the shaft a substantially oval shape. Referring back to FIG. 16, the rear opening 84 of the body 52 is preferably shaped to allow a shaft 58 of complimentary shape to pass through the rear opening. The rear opening 84 is preferably shaped to inhibit rotation of the shaft 58 within the body 52. The width of the hollow portion of the shaft 58 is slightly greater than the diameter of the driver 56, thereby allowing the driver to freely pass through the shaft. The shaft 58 may also include a knob 96 at an end of the shaft, as depicted in FIG. 17. The knob 96 may be a threaded nut which is screwed onto the shaft 58. The knob 96 may be used to position the shaft 58 within the body 52.

The shaft 58 preferably includes a tip 80 proximate an end of the shaft which is adapted to hold the connector 20. The tip 80 is preferably located at the end of the shaft 58 which extends from the front 81 of the body 52. FIG. 18 depicts a preferred embodiment of the tip 80. The tip 80 may be slightly larger than the diameter of the shaft 58. The tip 80 preferably includes two indentations 78 running along the outside surface of the tip. The indentations 78 are preferably oriented on opposing sides of the tip 80. The indentations 78 are preferably sized such that the width of the indentations are substantially greater than the width of the cable 10. The depth of the indentations 78 is preferably tapered, becoming shallower in a direction from the end of the shaft 58 toward the body 52.

The tip 80 may include a recessed opening which is adapted to couple with the connector 20. The front of the tip 80 is depicted in FIG. 19. The front of the tip 80 preferably contains a first slot 96 and a second slot 98. The first slot 96 preferably runs across the end of the tip 80, in the plane of the tip 80 formed by the two indentations 78. The second slot 98 preferably runs in a substantially perpendicular orientation to the first slot 96. The depth of the second slot 98 may be substantially greater than the depth of the first slot 96. The connector 20 may be mounted within the tip 80 such that the ducts 26 are oriented toward the indentations 78 of the tip. This arrangement preferably allows the cable 10 to freely pass through the connector 20 and along the indentations 78 while the connector 20 is mounted within the tip 80.

Figure 20:
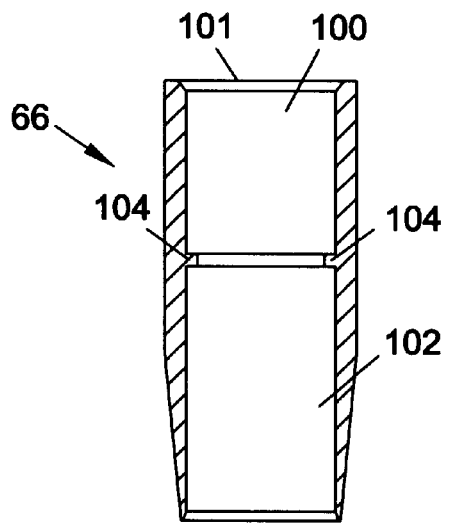
FIG. 20 depicts a cross-sectional view of a bushing cover of the tensioner as viewed from the side of the bushing cover.
Figure 21:
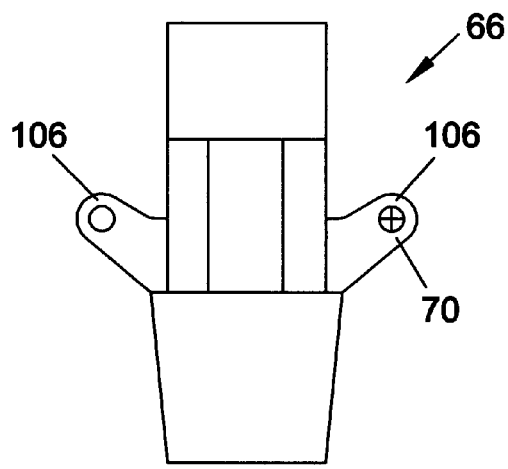
FIG. 21 depicts a side view of the bushing cover.
Figure 22:
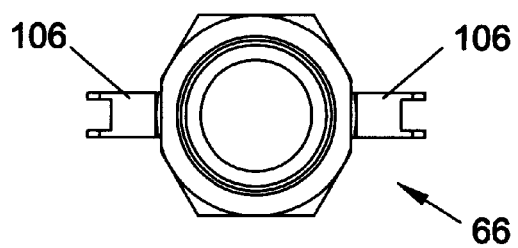
FIG. 22 depicts a top view of the bushing cover.

The body 52 may also include a substantially cylindrical and hollow bushing cover 66, as depicted in FIGS. 20, 21, and 22. The bushing cover 66 preferably includes an upper chamber 100, a lower chamber 102, a divider 104 and two arms 106. The upper chamber 100 is preferably sized such that the bushing cover 66 may be inserted over the bushing holder 86, as depicted in FIG. 17. The distance between the divider 104 and the top 101 of the bushing cover 66 may be substantially less than the distance that bushing holder 86 extends out from the body 52. The distance is set such that a space may exist between the bushing cover 66 and the front edge 81 of the body 52. The divider 104 preferably extends partially into the interior of the bushing cover 66, at a distance allowing the shaft 58 to pass through the bushing cover. The lower chamber 102 is preferably sized to allow the bushing 60 and the bushing spring 90 to be inserted together within the chamber, as depicted in FIG. 17. The arms 106 preferably extend from opposing sides of the bushing cover 66. The end of each arm 106 is preferably shaped into a substantially U-shaped groove, as depicted in FIG. 22. The bushing spring 90 is preferably sized to fit within the lower chamber 102. The bushing spring 90 is preferably sized to fit over the bushing 60.

Referring back to FIG. 17, the body 52 may include a substantially cylindrical and hollow bushing 60. It is preferred that the width of the hollow portion of the bushing 60 and the diameter of the shaft 58 be substantially equal. The shape of the hollow portion is preferably complimentary to the shape of the shaft 58. The hollow section may extend through the longitudinal axis of the bushing 60. The bushing 60 is preferably mounted within the bushing holder 86. The engagement of the bushing 60 with the shaft 58, while the bushing 60 is mounted within the bushing holder 86, preferably minimizes the lateral movement of the shaft within the body 52. The bushing holder 86 preferably contains female threading. The bushing 60 may include a threaded end, sized to fit the female threading of the bushing holder 86. The threaded end of the bushing 60 preferably engages the bushing holder 86 such that rotation of the bushing in a tightening direction moves the threaded end into the bushing holder.

The bushing 60 is preferably adapted to hold the bushing cover 66 onto the bushing holder 86, whereby the bushing cover is freely rotatable about the bushing holder. The bushing 60 preferably includes a flanged end. The bushing cover 66 and the bushing spring 90 are preferably placed on the bushing holder 86, such that the bushing spring lies within the lower chamber 102 of the bushing cover. The bushing spring 90 may rest against a front edge of the bushing holder 86. The bushing 60 may be fastened by screwing the threaded end into the threaded portion of the bushing holder 86. The flanged end of the bushing 60 preferably presses against the bushing cover 66 to hold the bushing cover against the bushing holder 86. The flanged end of the bushing 60 may also compress the bushing spring 90. The bushing spring 90 is adapted to prevent the bushing 60 from being overtightened. Overtightening of the bushing 60 might hinder or prevent rotation of the bushing cover 66 about the bushing holder 86.

Figure 23:
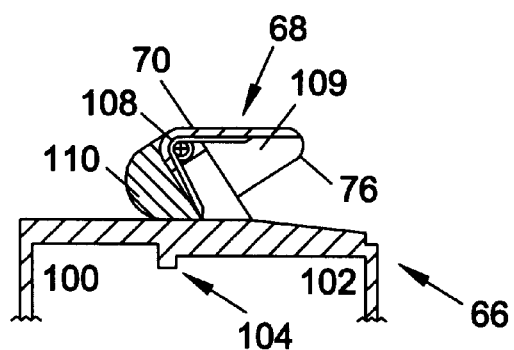
FIG. 23 depicts a cross-sectional partial view of the bushing cover with a cable clamp, as viewed from the side.

FIG. 23 depicts a portion of the bushing cover 66 which preferably includes a cable clamp 68 adapted to secure a cable 10 against a portion of the bushing cover. The bushing cover 66 preferably includes at least two cable clamps 68. The cable clamp 68 preferably includes a lever 76, a pin 70, and a spring 108. The lever 76 may include a substantially hollowed out portion 109 and a clamping portion 110. The lever 76 is preferably connected to an arm 106 of the bushing cover 66 with a substantially cylindrical pin 70. The pin 70 may extend through both the lever 76 and the U-shaped groove of the arm 106. The pin 70 may be mounted within the U-shaped groove of the arm 106 such that the lever 76 is pivotable about the pin.

The spring 108 preferably lies on the pin 70 and extends into the bushing cover 66 and along the lever 76. The spring 108 preferably extends into the hollow portion of the lever 76. In its resting position spring 108 preferably exerts a force against the inside edge of the hollow portion 109 such that the lever 76 is moved away from the bushing cover 66. When the hollow portion 109 extends away from the bushing cover 66, the clamping portion 110 is preferably disposed against the bushing cover. When pressed with sufficient force the lever 76 may pivot around the pin 70 such that the clamping portion 110 is no longer in contact with the bushing cover 66. The cable 10 may be passed under the lever 76 while the clamping portion 110 is in its raised position. The depression of the clamp lever 76 preferably compresses the spring 108. Removal of the force being applied to the lever 76 preferably allows the spring 108 to expand, thereby forcing the clamping portion 110 to return to the bushing cover 66. If a cable 10 is present when the force is released from the lever 76, the clamping portion 110 may become pressed against the cable, securing it in place against the bushing cover 66.

The arm spring 92 and the lock spring 94 may be compression springs. The spring 108 of the cable lock 68 is preferably a torsion spring. The bushing spring 90 is preferably a spring washer. The term "spring washer" in the context of this application is meant to mean a spring adapted to apply a predetermined force on adjacent members in an assembly.

Referring back to FIG. 17, the driver 56 may include a handle 114 attached to the elongated member 112 of the driver. The handle 114 is preferably a rod that is attached to the elongated member 112 in a perpendicular orientation, such that the driver 56 is substantially T-shaped. The handle 114 may be rotated to allow the driver 56 to be moved in tortionally. The elongated member 112 may be substantially longer than the shaft 58. The driver 56 preferably includes a head 116 adapted to engage the pin 22 of the connector 20. The head 116 is preferably located at an end of the elongated member 112 opposite to the handle 114. The shape of head 116 may be chosen to couple with a pin 22 of suitably recessed shape such that rotation of the handle may apply a tortional force to the pin. The head 116 is preferably hexagonal in shape for coupling with the hexagonal recess of the upper portion 46 of the opening 44 of the pin 22.

The shaft 58 may be substantially cylindrical and hollow. The hollow portion of the shaft 58 is preferably sized such that the elongated portion 112 of the driver 56 may be passed through the center of the shaft. The shaft 58 is configured such that the driver 56 may engage the pin 22 while the connector 20 is in contact with the shaft. The driver 56 may engage the pin 22 such that rotation of the driver 56 causes the pin to rotate. The driver 56 preferably engages the pin 22 such that rotation of the driver causes the pin 22 to rotate into a position which secures the cable 10 within the connector 20. Once the cable 10 has been clamped into this position, the driver 56 may engage the pin 22 such that rotation of the driver causes the pin to rotate into a position which allows movement of the cable within the connector 20.

The surgical procedure for implanting a surgical cable system around a portion of a human bone includes forming a loop around the desired portion, tensioning the cable 10, and securing the cable within the connector 20. The loop is preferably formed by threading the cable 10 through the connector 20, around a portion of the human bone and back through the connector. In an embodiment, the cable 10 may be looped around two or more adjacent vertebra. In another embodiment the cable 10 may be passed around a vertebra and a spinal fixation device. The spinal fixation device is adapted to immobilize a section of the human spine and may be a rod.

As depicted in FIG. 7, the cable 10 may be passed through a duct 26 of the connector 20, around a portion of the human bone, and back through a different duct 26. In an embodiment, the cable 10 may be threaded through the connector 20 exiting from the rear face 33 of the connector body 24. After encircling a bone member the cable 10 may reenter the connector body 24 from the front face 35. In another embodiment, depicted in FIG. 8, the cable 10 may be threaded through the connector 20 exiting from the rear face 33 of the connector body 24. After encircling a bone member the cable 10 may reenter the connector body 24 from the rear face 33, forming a loop around the bone member. The ends of the cable 10 may extend out from the connector body 24. The ends may be in a substantially parallel orientation with respect to each other.

In another embodiment, the cable 10 may include tip 16, as depicted in FIG. 1. Referring again to FIG. 7, the tip 16 is preferably of a diameter that is substantially larger than the diameter of a duct 26. The tip 16 preferably inhibits the cable 10 from passing completely through the duct 26. The cable 10 may be threaded through the connector 20, exiting from the rear face 33 of the connector body 24. The cable 10 is preferably threaded through the connector body 24 until the tip 16 is disposed against the front face 34 of the connector body 24. After encircling a bone member, the cable 10 may reenter the connector body 24 from the front face 35. In another embodiment, the cable 10 may reenter the connector body 24 from the rear face 33 of the connector body. As the cable 10 is tensioned, the tip 16 may be disposed against the front face 35 of the connector body 24. The tip 16 may remain disposed against the face of the connector body 24 until the tension of the cable 10 is released.

In an alternate embodiment, (referring to FIG. 13) the tip 16 is preferably of a diameter that is substantially larger than the diameter of an opening 44 of pin 22. The tip 16 preferably inhibits the cable 10 from passing completely through the opening 44. The cable 10 is preferably threaded through the opening 44 until the tip 16 is disposed against the lower portion 48 of the opening. After encircling a human bone member, the cable 10 may be passed into the connector body 24 through one of the ducts 26. The pin 22 is preferably oriented to allow this passage of the cable 10 through one of the ducts 26. As the cable 10 is tensioned, the tip 16 may be disposed against lower portion 48 of the opening 44. The tip 16 may remain disposed against the lower portion 48 of the opening 44 until the tension of the cable 10 is released.

A tensioner 50 may be used to increase the tension on a cable 10 after it has been encircled around a human bone member. The preferred embodiment of the tensioner 50 is illustrated in FIG. 14. The tensioner 50 may be prepared to receive the connector 20 by positioning the shaft 58 such that the tip 80 is positioned proximate to the front of the bushing 60. The shaft 58 may be positionable within the body 52 while the lock tab 62 is in a forward position. The lock tab 62 may be moved into the forward position by applying pressure to the rear face of the lock tab 62. Pressure on the lock tab 62 may be released allowing the lock tab to move away from the tensioner body 52. In this released position the lock tab 62 may prevent the rearward movement of the shaft 58.

After the cable 10 is looped around a human bone member and through the connector 20, the connector may be engaged by the tip 80 of the tensioner 50. The connector 20 is engaged by the tip 80 such that the front and rear faces of the connector are aligned with the indentations 78 (see FIG. 19). The top of the connector 20 may be substantially positioned within the tip 80. The pin 22 may be mounted within the connector body 24, and the connector body may be engaged by the tip 80.

A cable end is preferably positioned along the indentations 78 of the tip 80. The cable end is preferably clamped to the tensioner 50 by the cable clamp 68. The clamping portion 110 of the cable clamp 68 may be disposed against the side of the bushing cover 66 while in the resting position. When pressed with sufficient force the lever 76 may pivot around the arm pin 72 such that the clamping portion 110 is no longer in contact with the bushing cover 66. The cable 10 may be passed under the lever 76 while the clamping portion 110 is raised. Removal of the force being applied to the lever 76 preferably causes the clamping portion 110 to move toward the bushing cover 66. As a result, the clamping portion 110 may become pressed against the cable, thereby securing it in place against the bushing cover 66. In an embodiment, one end of the cable 10 is preferably secured to the bushing cover 66, using the cable clamps 68. In another embodiment, both ends of the cable 10 are preferably secured to the bushing cover 66.

Pressure may then be applied to the arm 54 of the tensioner 50 to pivot the arm around the arm pin 72 such that the arm moves in a direction toward the body 52 of the tensioner 50. Movement of the arm 54 toward the body 52 may be accompanied by movement of the shaft 58 away from the body 52. The angle to which the arm 54 is pivoted may determine the distance the shaft 58 extends from the body 52. When the pressure on the arm 54 is released, the arm preferably moves away from the body 52. Movement of the arm 54 away from the body 52 preferably does not effect the position of the shaft 58. With the cable 10 secured to the tensioner 50, movement of the shaft 58 away from the body 52 preferably pulls the cable 10 through the connector 20 in a direction away from the connector. As a result, the tension on the cable 10 preferably increases. The arm 54 may be repeatedly pressured and released as many times as necessary to achieve the desired tension.

In one embodiment, a pin 22 may be inserted into the connector body 24, after the cable 10 has been tensioned, to secure the cable within the connector 20. The driver 56 may be used to insert the pin 22 into the connector body 24. In an alternate embodiment, the pin 22 may be placed in the connector body 24 prior to tensioning the cable 10. The pin 22 may be positioned within the tip 80. The driver 56 may be inserted through the center of the shaft 58 until it engages the pin 22. The end of the driver 56 is preferably shaped to fit within the opening 44 of the pin 22. The rotation of the driver 56 may be accompanied by rotation of the pin 22 while the driver is inserted within the opening 44. The pin 22 is preferably oriented such that the cable 10 may pass through one of the ducts 26. Rotation of the pin 22 may alter the orientation of the pin such that the pin secures a portion of the cable 10 within the connector body 24. The pin 22 is preferably rotated 90° into a securing orientation. Rotation of the pin 22 is preferably performed after the cable 10 has been tensioned. In this manner, the diver 56 may rotate the pin 22 to secure a portion of the cable 10 within the connector 20 without removing the connector from the tip 80.

After securing the cable 10 within the connector 20 the tensioner 50 may be disengaged from the connector. The cable 10 may be removed from the cable clamp 68 before disengaging the tensioner 50. To remove the cable 10, pressure may be applied to the lever 76, causing the lever to lift from the bushing cover 66. As a result, the securing force exerted by the clamping portion 110 is removed, allowing the cable 10 to be removed from under the clamping portion. After removal of the cable 10 from the cable clamps 68, the connector 20 may then be removed from the tip 80 of the tensioner 50.

In an embodiment, the cable 10 may need to be retensioned after the connector 20 has been removed from the tensioner 50. In this situation, the connector 20 may be reinserted into the tip 80 of the tensioner 50. The cable 10 may be secured against the tensioner 50 with the cable clamp 68 of the tensioner 50. The driver 56 may be inserted into the opening 44 of the pin 22. Under these circumstances the pin 22 may be rotated by the driver 56 to an orientation which allows movement of the cable 10 through the connector body 24. The cable 10 may be retensioned by operation of the tensioner arm 54. When the desired tension is achieved, the cable 10 may be secured by the rotation of the pin 22 within the connector 20.

FURTHER IMPROVEMENTS

Figure 24:
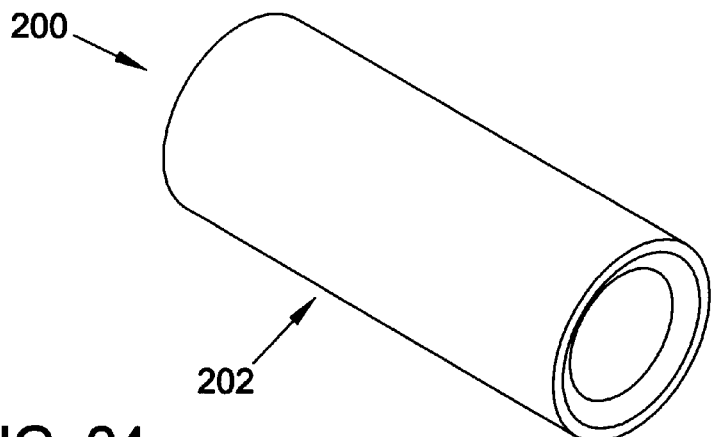
FIG. 24 depicts a perspective view of an eyelet including a substantially elongated eyelet member.
Figure 25:
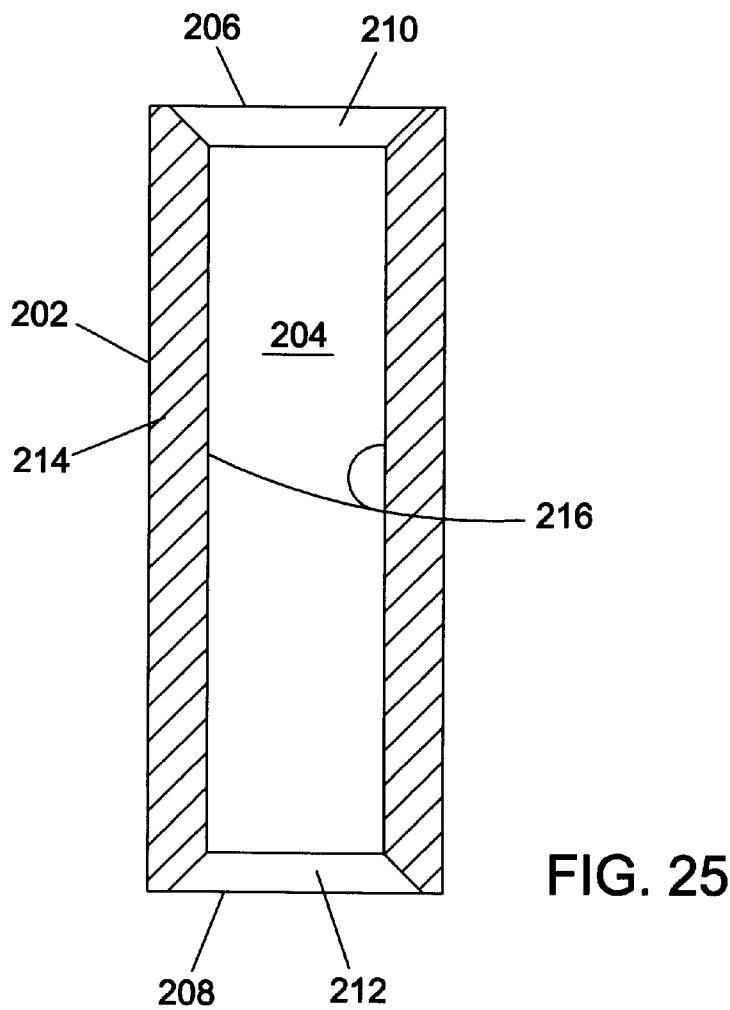
FIG. 25 depicts a cross-sectional view of the eyelet of FIG. 24.

FIG. 24 depicts an embodiment of an eyelet. Eyelet 200 preferably includes substantially elongated eyelet member 202. Eyelet member 202 is preferably formed of titanium, stainless steel, ceramic, plastic, polymer, composite material, or other biocompatible material. Eyelet member 202 is preferably configured to fit into a cable opening formed in a portion of a bone (not pictured) such that a cable (not pictured) (e.g., cable 10 of FIG. 2) may be passed around the bone portion without contacting the bone portion adjacent the cable opening. FIG. 25 depicts a longitudinal cross-sectional view of eyelet member 202. Bore 204 extends longitudinally through eyelet member 202 between first end 206 and second end 208. Bore 204 includes first opening 210 at first end 206 and second opening 212 at second end 208. As pictured in FIGS. 24–25, eyelet member 202 and bore 204 are substantially cylindrical in shape (i.e., substantially circular in radial cross-section). Alternatively, eyelet member 202 and bore 204 may be other than substantially circular in radial cross-section (e.g., substantially square, rectangular, hexagonal, or elliptical). As pictured, eyelet member 202 and bore 204 are substantially of the same shape. Alternatively, eyelet member 202 and bore 204 may be of substantially different cross-sectional shapes.

Bore 204 may be of substantially uniform diameter throughout eyelet member 202. Preferably, inner surface 216 of bore 204 is contoured such that wear on a cable (not pictured) inserted into eyelet member 202 due to contact with and motion against lateral wall 214 at openings 210 and 212 of eyelet member 202 may be minimized. As pictured in FIG. 25, inner surface 216 of bore 204 is beveled at first opening 210 and second opening 212. Alternatively, inner surface 216 may be rounded at openings 210 and 212.

In an embodiment, at least one of first end 206 and second end 208 may be deformable. A width of a deformable end may be greater following deformation (not pictured) than prior to deformation. Bore 204 may include a borehole (not pictured) through the deformed end to allow passage of a cable through the deformed end. Alternatively, eyelet member 202 may be non-deformable.

Figure 26:
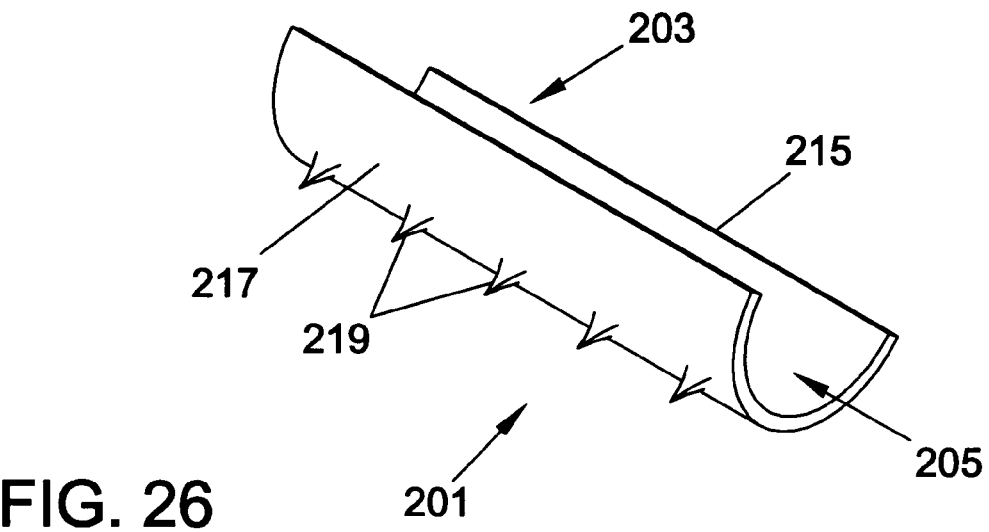
FIG. 26 depicts a perspective view of an eyelet including a substantially elongated eyelet member with a partially enclosed bore.

Lateral wall 214 of eyelet member 202 as pictured in FIGS. 24–25 completely encloses bore 204. FIG. 26 depicts an alternative embodiment of an eyelet 201 in which lateral wall 215 of eyelet member 203 only partially encloses bore 205. As pictured, outer surface 217 of lateral wall 215 includes protrusions 219 configured to form an engagement with a surface of a cable opening formed in a bone (not pictured). Such protrusions 219 may be included on any eyelet, including but limited to the eyelets depicted in the other figures. Eyelet member 203 may be inserted into a cable opening that is substantially completely surrounded by bone. Alternatively, eyelet member 203 may be inserted into a cable opening that is formed substantially at a bone surface such that a portion of the cable opening is not surrounded by the bone portion.

Figure 27:
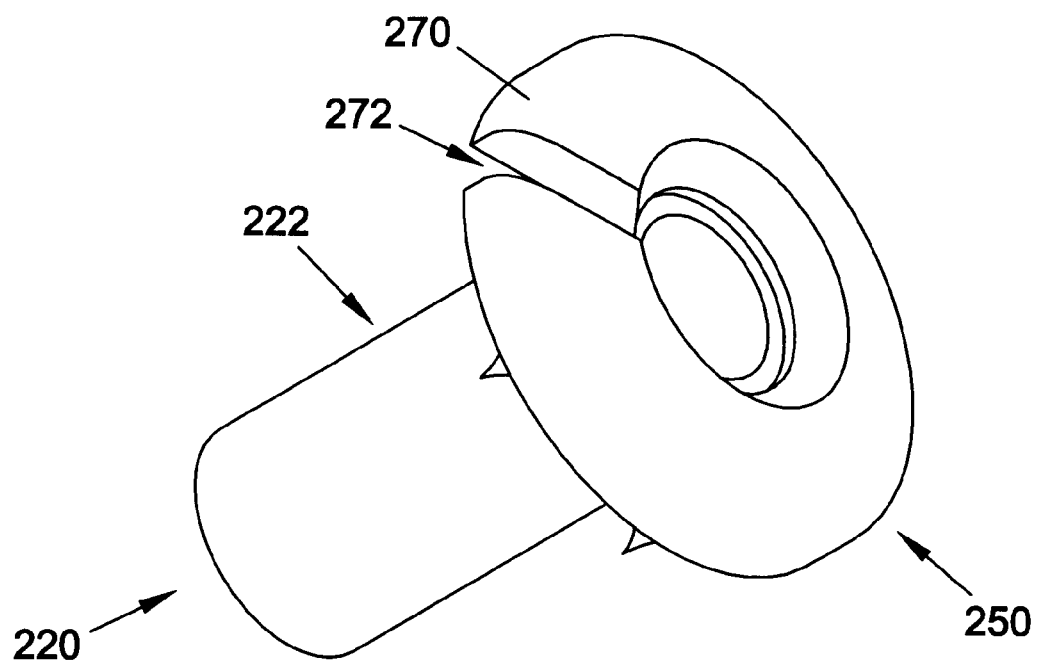
FIG. 27 depicts a perspective view of an eyelet including a substantially elongated eyelet member and an endpiece.
Figure 28:
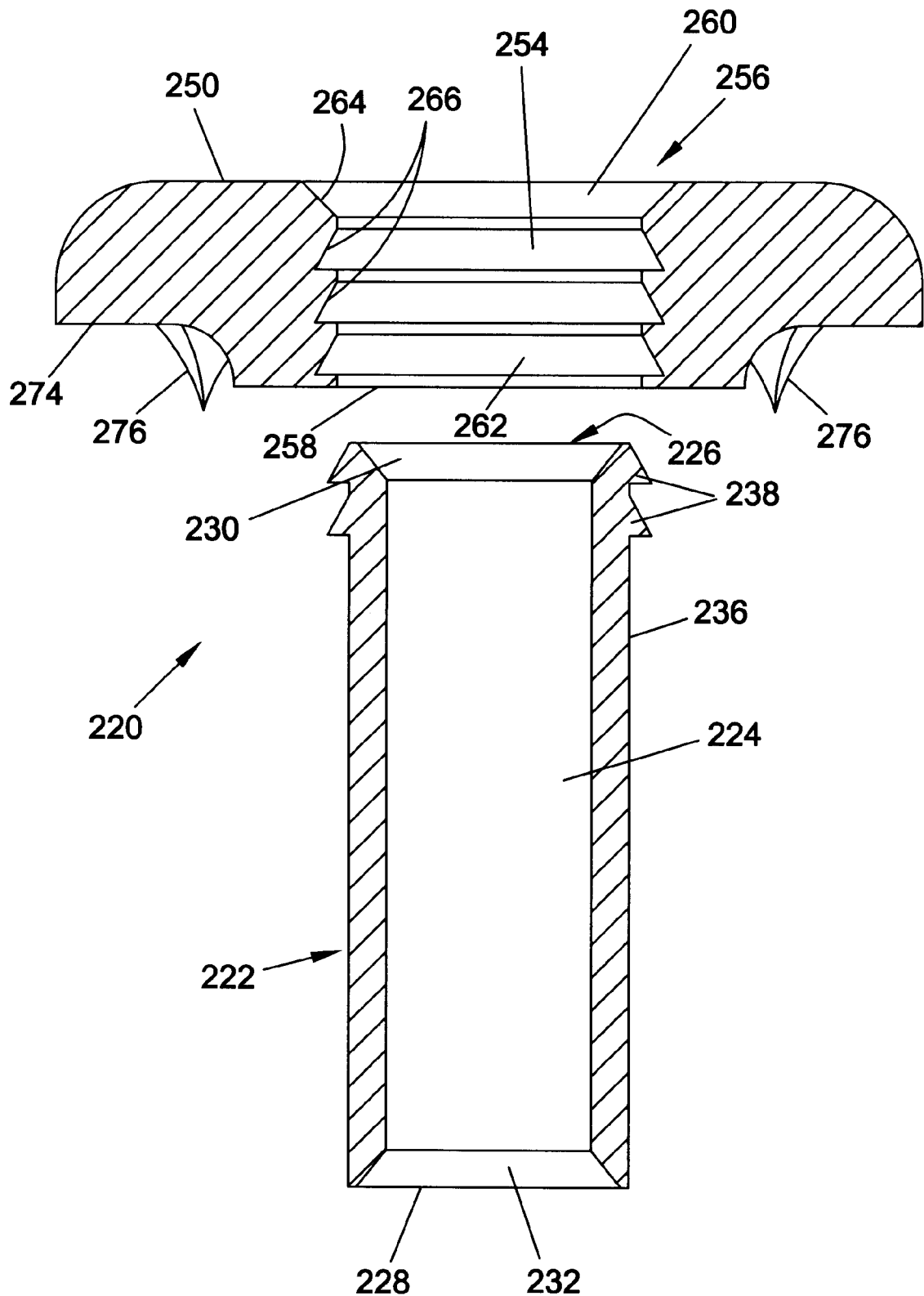
FIG. 28 depicts a cross-sectional view of the components of eyelet of FIG. 27.

FIG. 27 depicts an alternative embodiment of an eyelet for protecting a bone. Eyelet 220 includes substantially elongated eyelet member 222. Eyelet 220 is preferably formed of titanium, stainless steel, ceramic, plastic, polymer, composite material, or other biocompatible material. FIG. 28 depicts a longitudinal cross-sectional view of eyelet member 222. Bore 224 extends longitudinally through eyelet member 222 between first end 226 and second end 228. Bore 224 includes first opening 230 at first end 226 and second opening 232 at second end 228. As pictured in FIGS. 27–28, eyelet member 222 and bore 224 are substantially cylindrical in shape. Alternatively, eyelet member 222 and bore 224 may be other than substantially circular in radial cross-section (e.g., substantially square, rectangular, hexagonal, or elliptical). As pictured, eyelet member 222 and bore 224 are substantially of the same shape. Alternatively, eyelet member 222 and bore 224 may be of different cross-sectional shapes.

Eyelet 220 may further include endpiece 250. Endpiece 250 may be of a width greater than a width of eyelet member 222. FIG. 27 includes a longitudinal cross-sectional view of endpiece 250. Bore 254 extends longitudinally through endpiece 250 between first end 256 and second end 258. Bore 254 includes first opening 260 at first end 256 and second opening 262 at second end 258. Bore 254 may be of a width greater than a width of eyelet member 222. As pictured in FIGS. 27–28, endpiece 250 and bore 254 are substantially cylindrical in shape. Alternatively, endpiece 250 and bore 254 may be other than substantially circular in radial cross-section (e.g., substantially square, rectangular, hexagonal, or elliptical). As pictured, endpiece 250 and bore 254 are substantially of the same shape. Alternatively, endpiece 250 and bore 254 may be of different cross-sectional shapes. Additionally, endpiece 250 may be of a different radial cross-sectional shape than eyelet member 222.

Outer surface 236 of eyelet member 222 may include at least one projection 238; as pictured in FIG. 28, eyelet member 222 includes two projections. Projections 238 may be tapered such that a width of projections 238 increases with increasing distance from first end 226. Bore 254 of endpiece 250 may include inner surface 264. Inner surface 264 may include at least one groove 266; as pictured, inner surface 264 includes three grooves. Grooves 266 may be tapered such that a width of grooves 266 decreases with increasing distance from second opening 262 of endpiece 250.

First end 226 may be inserted into second opening 262 of bore 254 to form a fixable engagement between eyelet member 222 and endpiece 250. Projections 238 may be configured to fit into grooves 266 such that lateral motion of eyelet member 222 is inhibited with respect to endpiece 250. In an embodiment, endpiece 250 may include elongated opening 272 in lateral wall 270 (FIG. 27). Elongated opening 272 may allow a width of endpiece 250 to vary to facilitate formation of the fixable engagement between eyelet member 222 and endpiece 250 (i.e., allowing the width of endpiece 250 to vary may facilitate insertion of projections 238 into grooves 266).

Endpiece 250 may further include protrusions 276 from exterior surface 274. Protrusions 276 may be configured to form an engagement with a portion of a bone (not shown) during use such that movement of eyelet 220 with respect to the bone portion is inhibited during use. The engagement may prevent a cable (not pictured) threaded through eyelet 220 from contacting the bone portion. The engagement may further prevent motion (e.g., rotation) of eyelet 220 from damaging the bone portion.

In an embodiment, second end 228 may be deformable. A width of second end 228 may be greater following deformation (not pictured) than prior to deformation. Bore 234 may include a borehole (not pictured) through second end 228 following deformation to allow passage of a cable similar to cable 10 (FIG. 2) through deformed second end 228. Deformation of second end 228 may serve to further anchor eyelet 220 into the bone.

Figure 29:
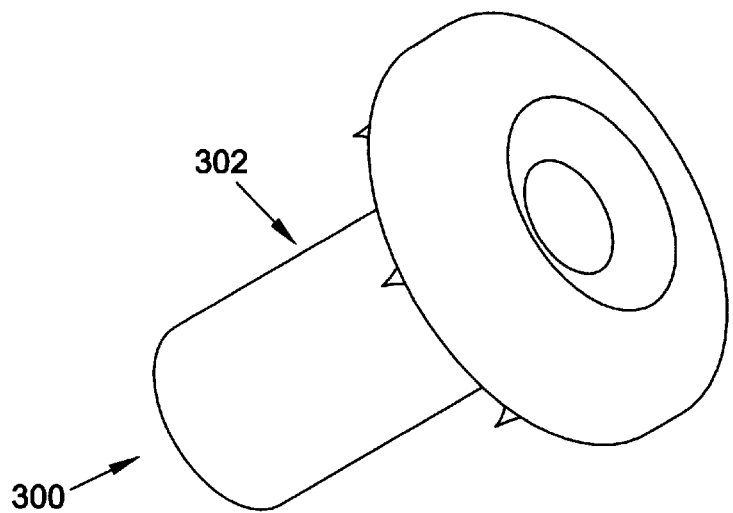
FIG. 29 depicts a perspective view of an eyelet including first and second portions of differing widths.
Figure 30:
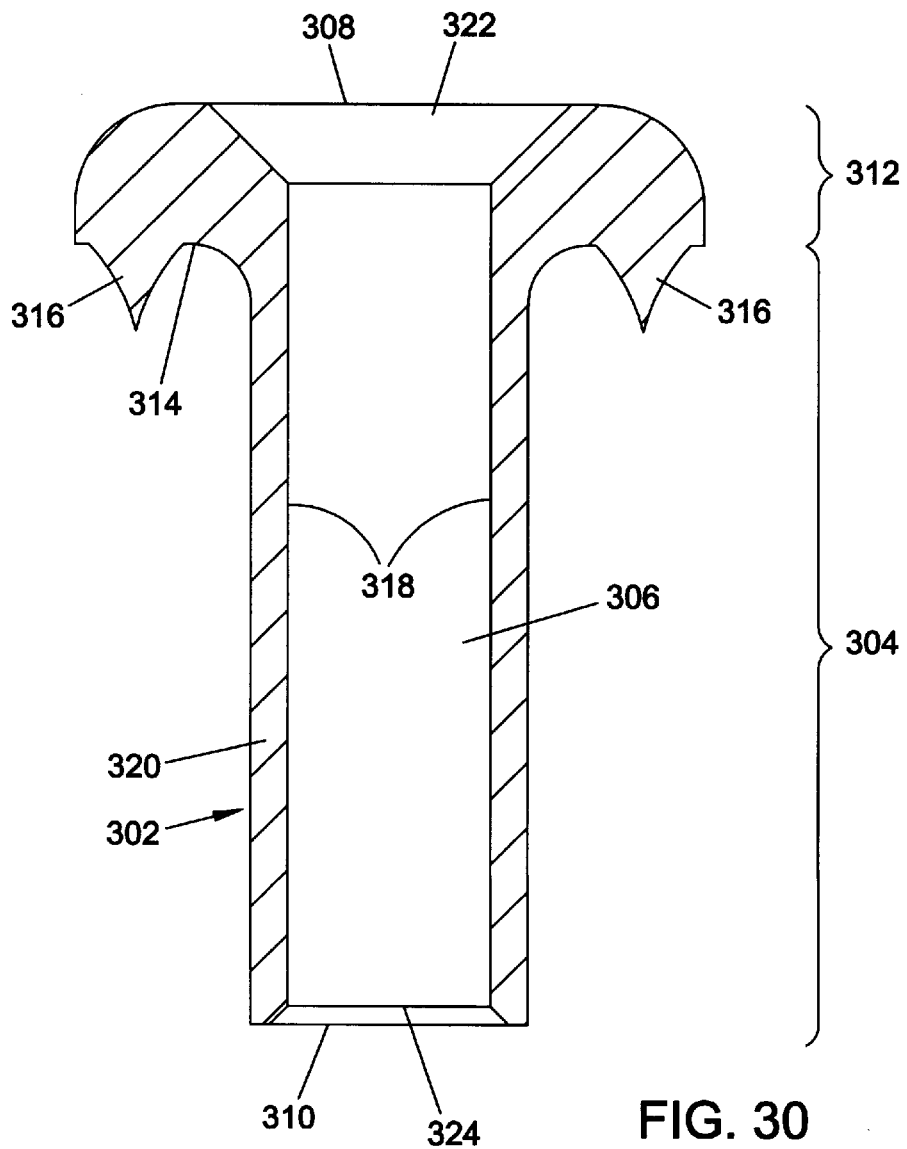
FIG. 30 depicts a cross-sectional view of the eyelet of FIG. 29.

An alternative embodiment of an eyelet for protecting a bone is depicted in FIG. 29. Eyelet 300 includes eyelet member 302. As shown in longitudinal cross-section in FIG. 30, substantially elongated first portion 304 of eyelet member 302 includes bore 306 extending between first end 308 and second end 310. Bore 306 passes through second portion 312 of eyelet member 302 at first end 308. A width of second portion 312 may be greater than a width of first portion 304. Eyelet 300 is preferable formed of titanium, stainless steel, ceramic, plastic, polymer, composite material, or other biocompatible material.

First portion 304, second portion 312, and bore 306 may all be of substantially the same radial cross-sectional shape. As depicted, first portion 302, second portion 312, and bore 306 are all substantially circular in radial cross-section. First portion 302, second portion 312, and bore 306 may, however, be other than circular (e.g., substantially square, rectangular, hexagonal, elliptical) in radial cross-section. First portion 302, second portion 312, and bore 306 also may be of different radial cross-sectional shapes from each other.

Second portion 312 of eyelet member 302 may further include protrusions 316 from exterior surface 314. Protrusions 316 may be configured to form an engagement with a portion of a bone (not shown) during use such that movement of eyelet 300 with respect to the bone portion is inhibited during use. The engagement may prevent a cable (not pictured) threaded through eyelet 300 from contacting the bone portion. The engagement may further prevent motion (e.g., rotation) of eyelet 300 from damaging the bone portion.

Bore 306 may be of uniform diameter throughout eyelet member 302. Preferably, inner surface 318 of bore 306 is contoured such that wear on a cable (not pictured) inserted into eyelet member 302 due to contact with and motion against lateral wall 320 at openings 322 and 324 of eyelet member 302 may be minimized. As pictured in FIG. 30, inner surface 318 of bore 306 is beveled at first opening 322 and second opening 324. Alternatively, inner surface 318 may be rounded at openings 322 and 324.

In an embodiment, second end 310 may be deformable. A width of second end 310 may be greater following deformation (not pictured) than prior to deformation. Bore 306 may include a borehole (not pictured) through deformed second end 310 to allow passage of a cable similar to cable 10 (FIG. 2) through deformed second end 310. Deformation of second end 310 may serve to further anchor eyelet 300 into the bone.

As pictured, eyelet member 302 is substantially rigid such that the dimensions of eyelet member 302 are substantially fixed. Alternatively, eyelet member may include a substantially elongated opening extending the length of lateral wall 320 and similar to opening 272 in endpiece 250 (FIG. 27). Such an opening may facilitate insertion of eyelet 300 into a cable opening formed in a portion of a bone (not shown) by allowing the width of the eyelet to be altered. Once inserted, the eyelet may expand to fit the cable opening. The tension of the eyelet against the cable opening may more securely hold the eyelet in the cable opening.

Figure 31:
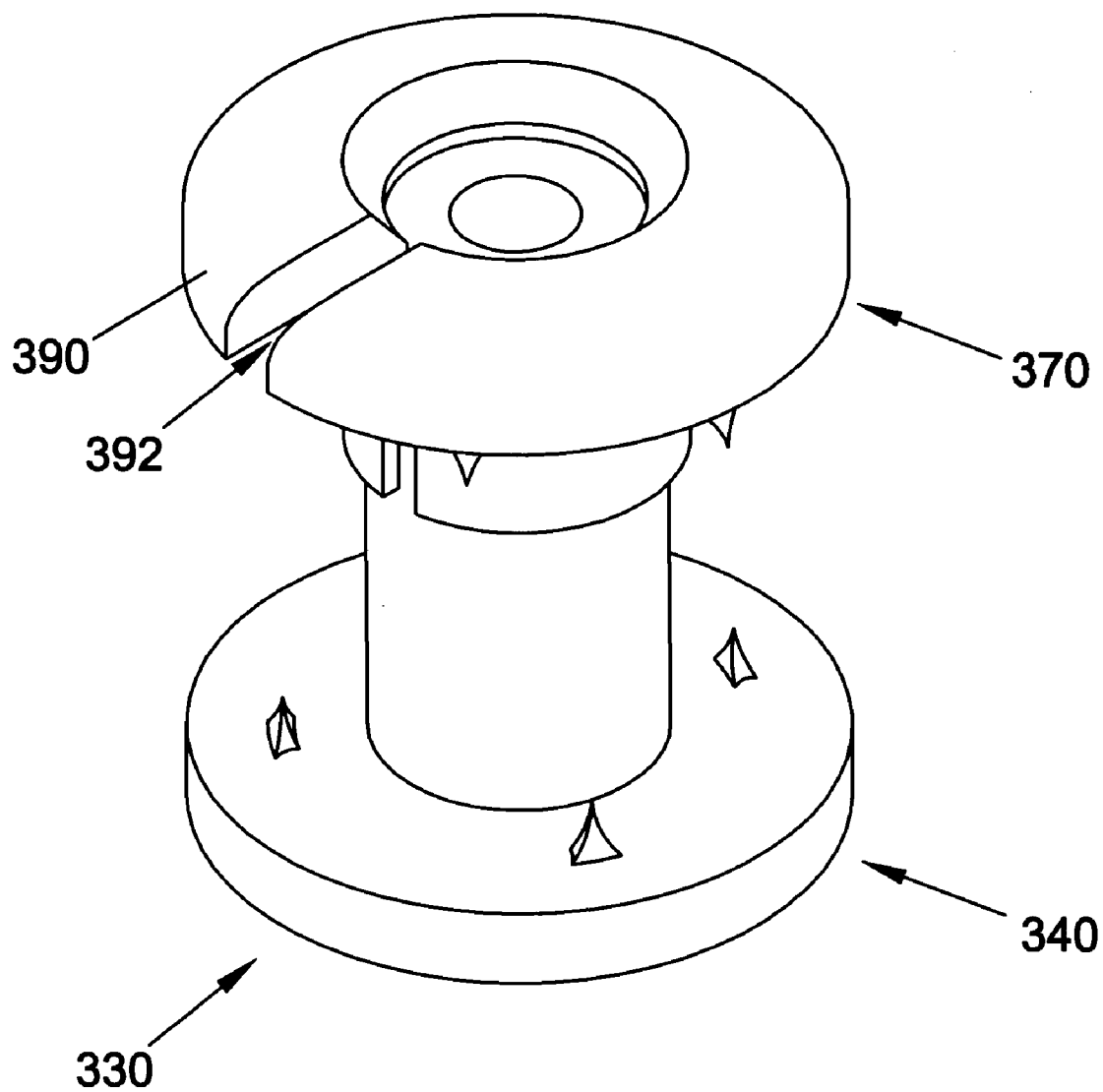
FIG. 31 depicts a perspective view of an eyelet including an eyelet member having first and second portions of differing widths and an endpiece.

An alternative embodiment of an eyelet for protecting a bone is depicted in FIG. 31. Eyelet 330 includes eyelet member 340 and endpiece 370. As shown in longitudinal cross-section in FIG. 32, substantially elongated first portion 342 of eyelet member 340 includes bore 346 extending between first end 348 and second end 350. Bore 346 also passes through second portion 344 of eyelet member 340 at second end 348. A width of second portion 344 may be greater than a width of first portion 342. Eyelet 330 is preferable formed of titanium, stainless steel, ceramic, plastic, polymer, composite material, or other biocompatible material.

First portion 342, second portion 344, and bore 346 may all be of substantially the same radial cross-sectional shape. As depicted, first portion 342, second portion 344, and bore 346 are all substantially circular in radial cross-section. First portion 342, second portion 344, and bore 346 may, however, be other than circular (e.g., substantially square, rectangular, hexagonal, elliptical) in radial cross-section. First portion 342, second portion 344, and bore 346 also may be of different radial cross-sectional shapes.

Figure 32:
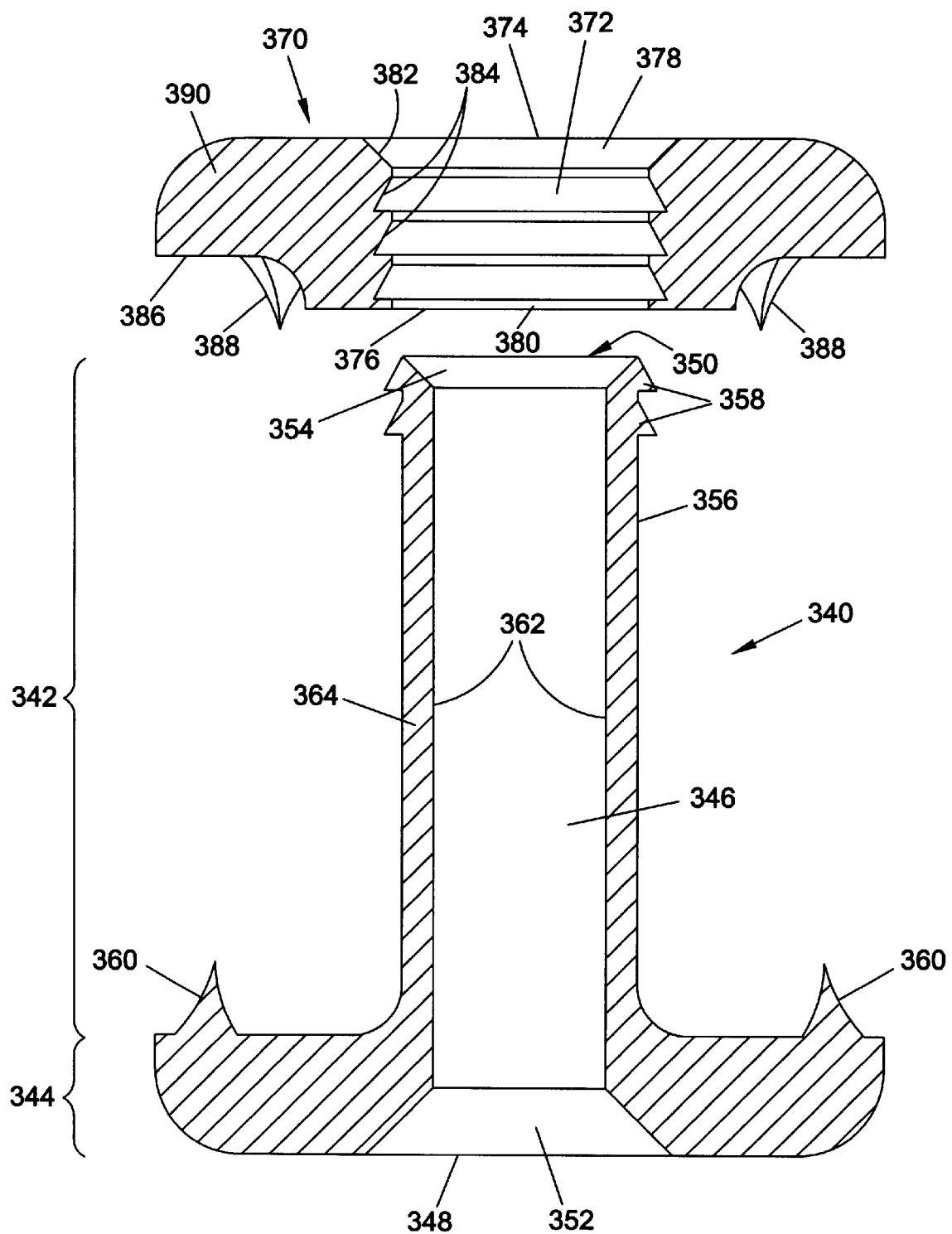
FIG. 32 depicts a cross-sectional view of the components of the eyelet of FIG. 31.

FIG. 32 includes a longitudinal cross-sectional view of endpiece 370. Endpiece 370 may be of a width greater than a width of eyelet member 330. Bore 372 extends longitudinally through endpiece 370 between first end 374 and second end 376. Bore 372 includes first opening 378 at first end 374 and second opening 380 at second end 376. Bore 372 may be of a width greater than a width of first portion 372 of eyelet member 370. As pictured in FIGS. 31–32, endpiece 370 and bore 372 are substantially cylindrical in shape. Alternatively, endpiece 370 and bore 372 may be other than substantially circular in radial cross-section (e.g., substantially square, rectangular, hexagonal, or elliptical). As pictured, endpiece 370 and bore 372 are substantially of the same shape. Alternatively, endpiece 370 and bore 372 may be of different cross-sectional shapes. Additionally, endpiece 370 may be of a different radial cross-sectional shape than eyelet member 340.

Outer surface 356 of eyelet member 340 may include at least one projection 358 at second end 350; as pictured in FIG. 32, eyelet member 340 includes two projections. Projections 358 may be tapered such that a width of projections 358 decreases with increasing distance from first end 348. Bore 346 of endpiece 370 may include inner surface 382. Inner surface 382 may include at least one groove 384; as pictured, inner surface 382 includes three grooves. Grooves 384 may be tapered such that a width of grooves 384 decreases with increasing distance from second opening 380 of endpiece 370.

Second end 350 of eyelet member 340 may be inserted into bore 372 of endpiece 370 to form a fixable engagement between eyelet member 340 and endpiece 370. Projections 358 may be configured to fit into grooves 384 such that lateral motion of eyelet member 340 is inhibited with respect to endpiece 370. In an embodiment, endpiece 370 may include elongated opening 392 in lateral wall 390. Elongated opening 392 may allow a width of endpiece 370 to vary to facilitate formation of the fixable engagement between eyelet member 340 and endpiece 370 (i.e., allowing the width of endpiece 370 to vary may facilitate insertion of projections 358 into grooves 384).

Eyelet member 340 may further include one or more protrusions from outer surface 356. Alternatively, endpiece 370 may further include one or more protrusions from exterior surface 386. As pictured in FIGS. 31–32, eyelet member 340 includes protrusions 360 from outer surface 356 and endpiece 370 includes protrusions 388 from exterior surface 386. Alternatively, neither eyelet member 340 nor endpiece may include protrusions. Protrusions 360 and/or 388 may be configured to form an engagement with a portion of a bone (not shown) during use such that movement of eyelet 330 with respect to the bone portion is inhibited during use. The engagement may prevent a cable (not pictured) threaded through eyelet 330 from contacting the bone portion. The engagement may further prevent motion (e.g., rotation) of eyelet 330 from damaging the bone portion.

First bore 346 may be of uniform diameter throughout eyelet member 340. Second bore 372 may be of uniform diameter throughout endpiece 370. Preferably, inner surface 362 of first bore 346 and inner surface 382 of second bore 372 are contoured such that wear on a cable (not pictured) inserted into eyelet member 330 due to contact with and motion against lateral wall 364 of eyelet member 340 at first opening 352 and contact with and motion against lateral wall 390 of endpiece 370 at first opening 378 may be minimized. As pictured in FIG. 32, inner surfaces 362 and 382 of first bore 346 and second bore 372, respectively, are beveled or smoothed at openings 352, 354, and 378. Alternatively, inner surfaces 362 and 382 may be rounded at openings 352, 354 and 378.

Figure 33:
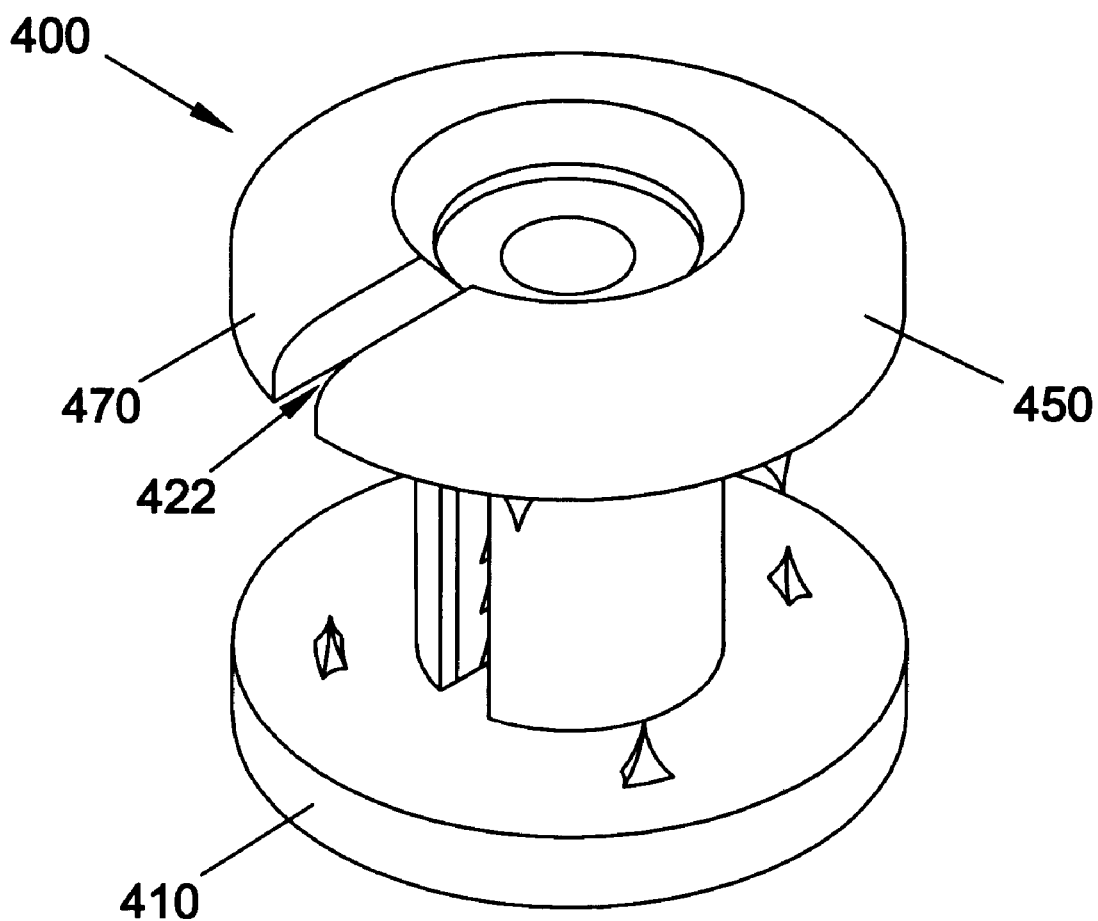
FIG. 33 depicts a perspective view of an eyelet including two eyelet members, each of which has first and second portions of differing widths.

An alternative embodiment of an eyelet for protecting a bone is depicted in FIG. 33. Eyelet 400 includes first eyelet member 410 and second eyelet member 450. As shown in longitudinal cross-section in FIG. 34, substantially elongated first portion 412 of first eyelet member 410 includes first bore 416 extending between first end 418 and second end 420. First bore 416 also passes through second portion 414 of first eyelet member 410 at first end 418. A width of second portion 414 may be greater than a width of first portion 412. Substantially elongated third portion 452 of second eyelet member 450 includes second bore 456 extending between third end 458 and fourth end 460. Second bore 456 also passes through second portion 454 of second eyelet member 450 at third end 458. A width of third portion 454 may be greater than a width of fourth portion 452. Eyelet 400 is preferable formed of titanium, stainless steel, ceramic, plastic, polymer, composite material, or other biocompatible material.

First portion 412, second portion 414, and first bore 416 may all be of substantially the same radial cross-sectional shape. As depicted, first portion 412, second portion 414, and first bore 416 are all substantially circular in radial cross-section. First portion 412, second portion 414, and first bore 416 may, however, be other than circular (e.g., substantially square, rectangular, hexagonal, elliptical) in radial cross-section. First portion 412, second portion 414, and first bore 416 also may be of different radial cross-sectional shapes. Third portion 452, fourth portion 454, and second bore 456 may all be of substantially the same radial cross-sectional shape. As depicted, third portion 452, fourth portion 454, and second bore 456 are all substantially circular in radial cross-section. Third portion 452, fourth portion 454, and second bore 456 may, however, be other than circular in radial cross-section. Third portion 452, fourth portion 454, and bore 456 also may be of different radial cross-sectional shapes.

Figure 34:
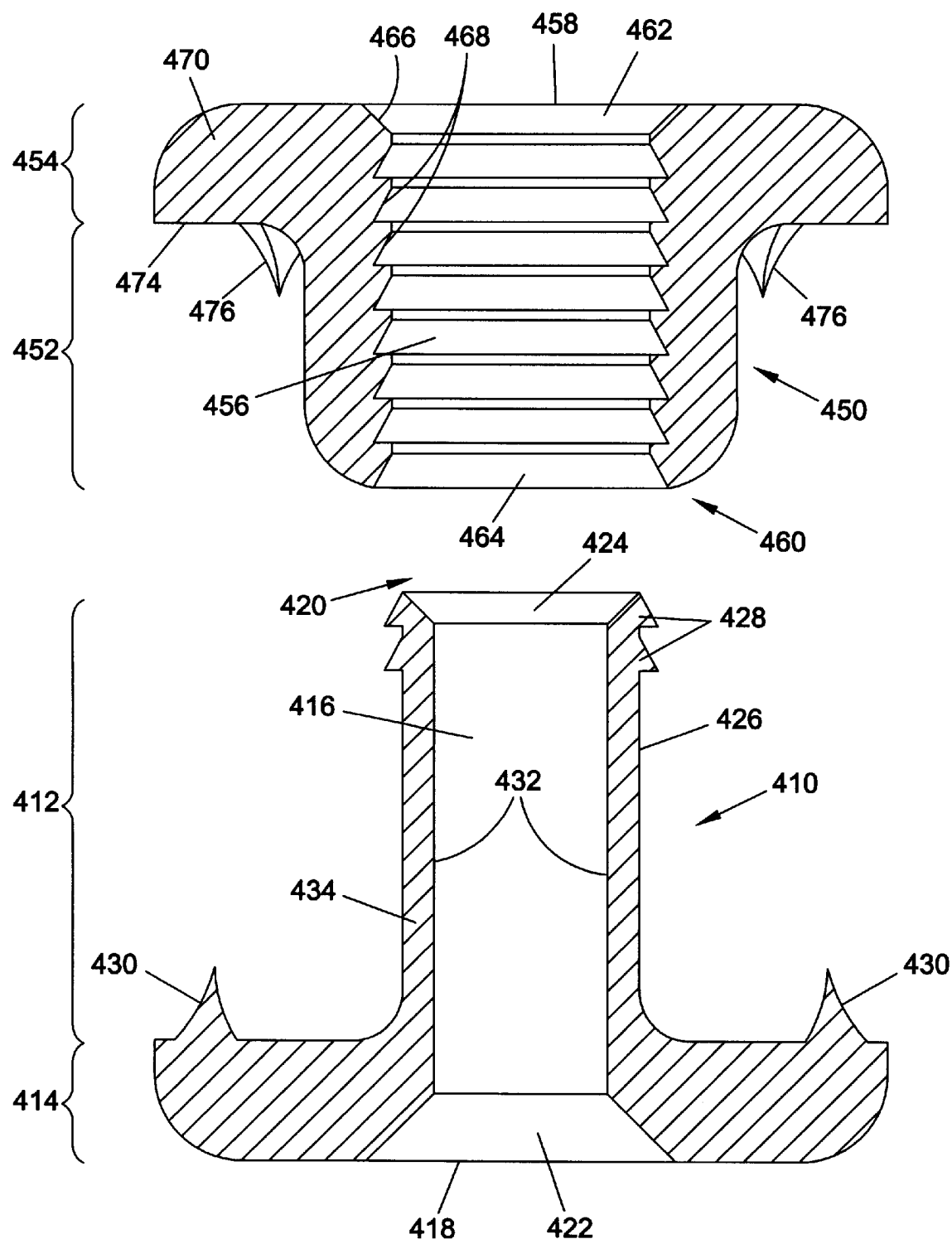
FIG. 34 depicts a cross-sectional view of the components of the eyelet of FIG. 33.

Outer surface 426 of first eyelet member 410 may include at least one projection 428; as pictured in FIG. 34, first eyelet member 410 includes two projections. Projections 428 may be tapered such that a width of projections 428 decreases with increasing distance from first end 418. Second bore 456 of second eyelet member 450 may include inner surface 466. Inner surface 466 may include at least one groove 468; as pictured, inner surface 466 includes seven grooves. Grooves 468 may be tapered such that a width of grooves 468 increases with increasing distance from third end 462 of second eyelet member 450.

Figure 35:
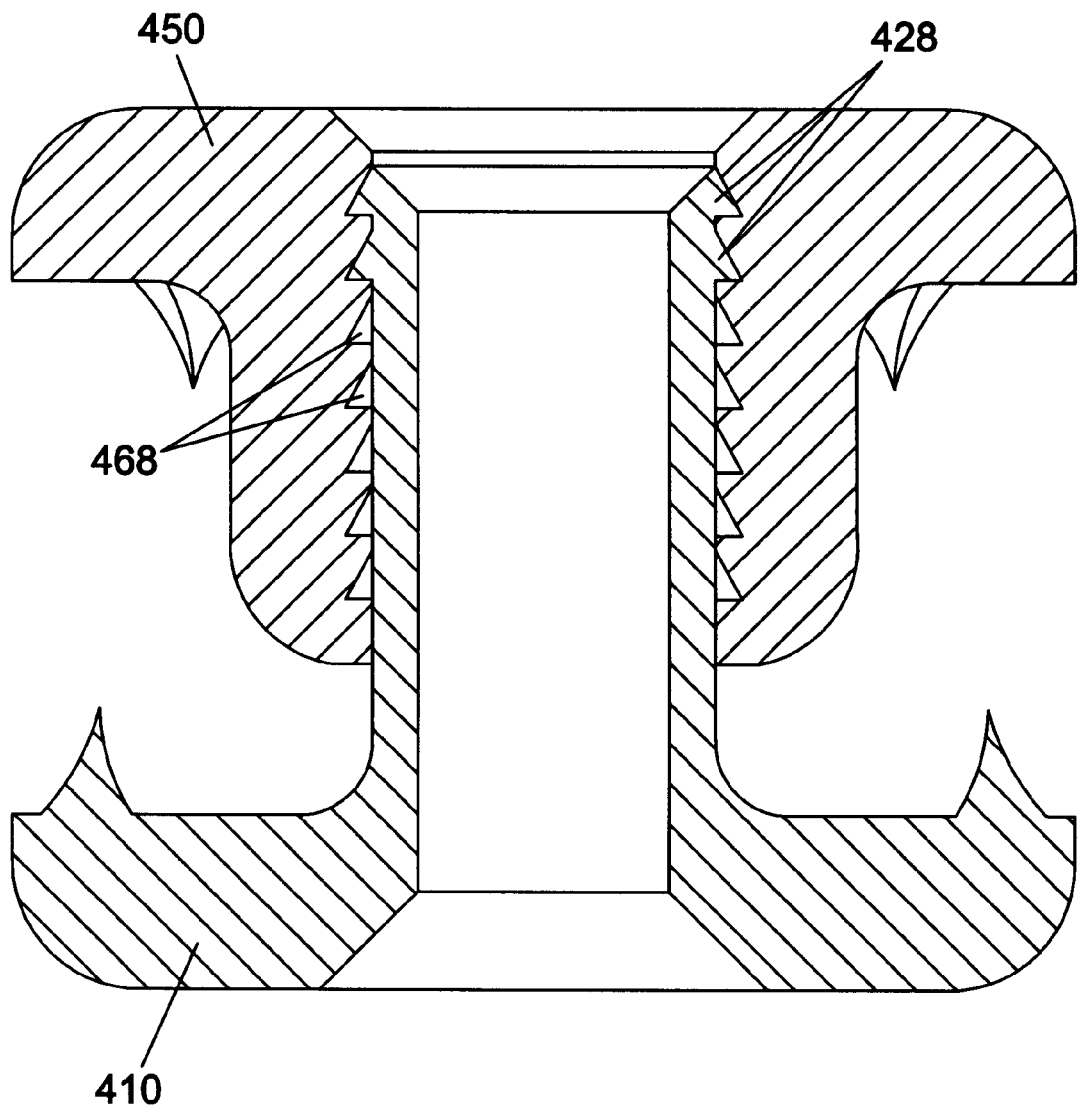
FIG. 35 depicts a cross-sectional view of the components of the eyelet of FIG. 33 in a fixable engagement.

Second end 420 may be inserted into fourth opening 464 at fourth end 460 to form a fixable engagement between first eyelet member 410 and second eyelet member 450 as show in FIG. 35. Projections 428 may be configured to fit into grooves 468 such that lateral motion of first eyelet member 410 is inhibited with respect to second eyelet member 450. In an embodiment, second eyelet member 450 may include elongated opening 472 in lateral wall 470 (FIG. 33). Elongated opening 472 may allow a width of second eyelet member 450 to vary to facilitate formation of the fixable engagement between first eyelet member 410 and second eyelet member 450 (i.e., allowing the width of second eyelet member 450 to vary may facilitate insertion of projections 428 into grooves 464).

First bore 416 may be of uniform diameter throughout first eyelet member 410. Second bore 456 may be of uniform diameter throughout second eyelet member 450. Preferably, inner surfaces 432 and 466 of first and second bores 416 and 456, respectively, are contoured at first and third openings 422 and 458, respectively, such that wear on a cable inserted into eyelet 400 due to contact with and motion against lateral walls 434 and 470, respectively, may be minimized. As pictured in FIG. 34, inner surfaces 432 and 466 are beveled at openings 422, 424, and 462. Alternatively, inner surfaces 432 and 466 may be rounded at openings 422, 424, and 462.

As pictured, first eyelet member 410 includes first protrusions 430 from exterior surface 426 and second eyelet member 450 includes second protrusions 476 from exterior surface 474. Alternatively, only one of first eyelet member 410 and second eyelet member 450 may include protrusions from an exterior surface. Alternatively, neither first eyelet member 410 nor second eyelet member 450 may include protrusions from an exterior surface. Protrusions 430 and 474 may be configured to form an engagement with a portion of a bone during use such that movement of eyelet 400 with respect to the bone portion is inhibited during use. The engagement may prevent a cable threaded through eyelet 400 from contacting the bone portion. The engagement may further prevent motion (e.g., rotation) of eyelet 400 from damaging the bone portion.

Figure 36:
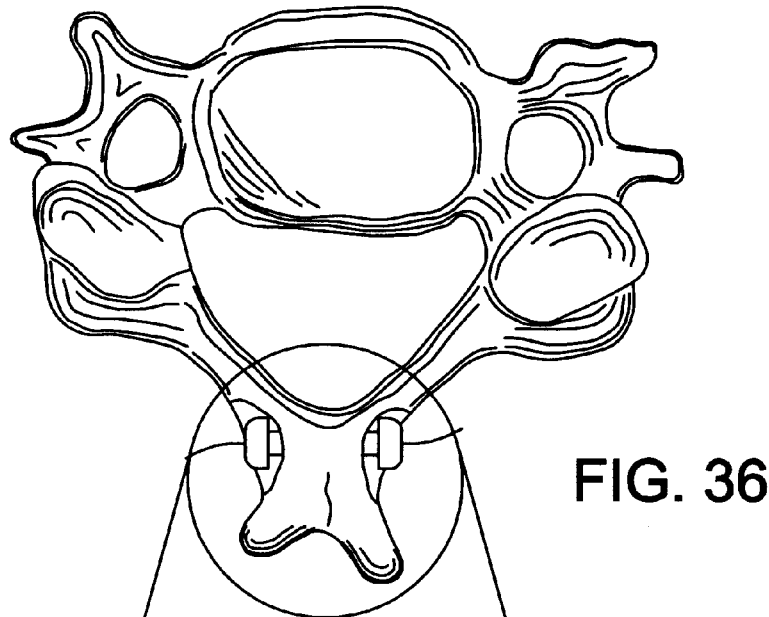
FIG. 36 depicts a top view of a vertebra in which a cable system including the eyelet of FIG. 33 has been inserted.
Figure 37:
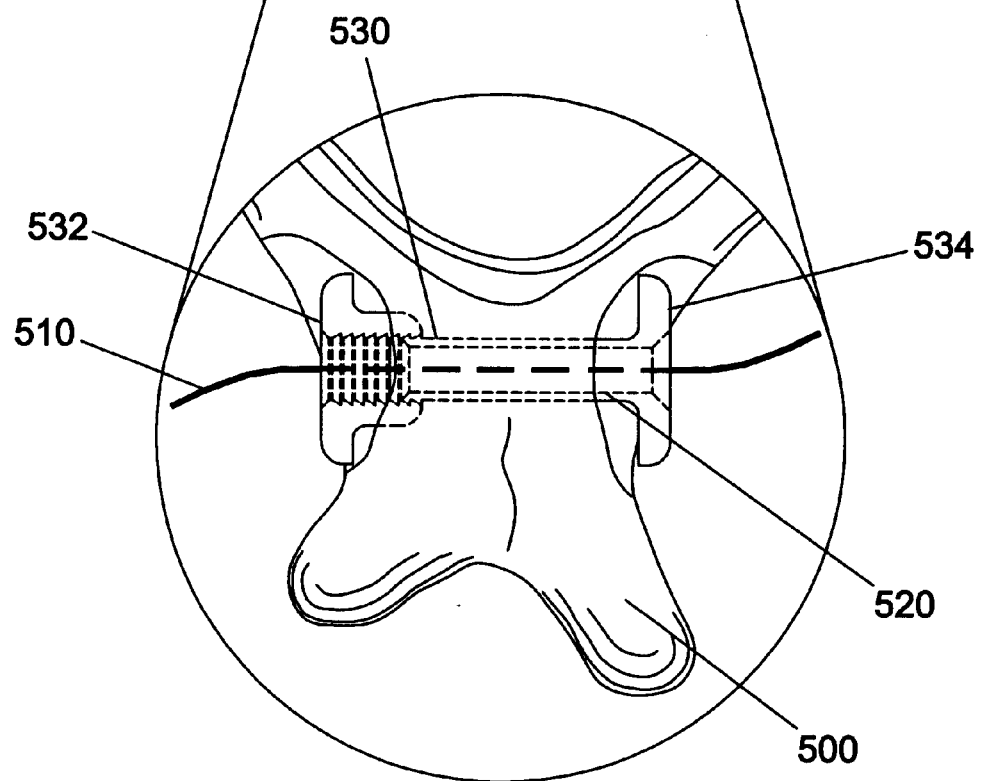
FIG. 37 depicts a detailed view of a portion of the vertebra and cable system of FIG. 36.

FIG. 36 depicts a top view of a surgical cable threaded through a vertebra. FIG. 37 is a detailed view of a portion of FIG. 36. Surgical cable 510 is threaded through cable opening 520 formed in vertebra 500. Eyelet 530 has been inserted into cable opening 520 and cable 510 then inserted through eyelet 530. As pictured, eyelet 530 includes first and second eyelet members 532 and 534 similar to eyelet members 410 and 450 of FIG. 34. Portions of eyelet 530 and cable 510 obscured by vertebra 500 are shown in phantom in FIG. 37. Interior portions of eyelet members 532 and 534 are also shown in phantom to illustrate the fixable engagement formed between the eyelet members.

The systems, eyelets, and methods described herein tend to distribute the force exerted by the cable to the eyelet, and the eyelet then tends to distribute such force over larger surface areas of the bone. Thus, instead of the cable applying force directly to the bone over a relatively small area (and thus causing possible breakage or wear of the bone), the cable applies force to the eyelet and the eyelet then transfers this force over a relatively large area of the bone. As a result, the force per area exerted by the cable on the bone is reduced, thereby reducing bone breakage and wear.

Unprotected cable will tend to "saw" or cause wear on the bone when the cable moves (such movement may occur when the patient moves). An advantage of the systems, eyelets, and methods described herein is that contact of the cable to the bone may be reduced (e.g., at bone stress points), and thus bone "sawing" or wear will be lessened or eliminated.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. An eyelet for protecting a bone from a surgical cable, comprising:
    a substantially elongated first eyelet member forming a bore for housing a portion of the surgical cable, the eyelet member comprising a width, a first end, a second end opposite the first end, and a biocompatible material, the eyelet member being at least partially positionable into a cable opening formed in the bone during use, wherein the bore extends through the eyelet member being positionable into a cable opening formed in the bone during use;
    a substantially elongated second eyelet member forming a bore for housing a portion of the surgical cable, said second eyelet member comprising a biocompatible material, said second eyelet member being at least partially positionable into the cable opening during use, and said second eyelet member configured to couple to a portion of the first eyelet member during use; and
    a slot in a wall of the second eyelet member, said slot extending from the bore in the second eyelet member to an outside surface of the second eyelet member, and said slot extending from a first end of the second eyelet member toward a second end of the second eyelet member;
    and wherein the eyelet is configured to substantially surround a portion of the surgical cable during use to substantially inhibit the portion of surgical cable housed within the eyelet from contacting the bone.

2. The eyelet of claim 1, further comprising an outer surface between the first end and the second end of the first eyelet member, and protrusions extending from the outer surface, wherein the protrusions are configured to extend into the bone to form an engagement with the bone during use.

3. The eyelet of claim 1 wherein a surface of the first eyelet member abuts against bone adjacent to the cable opening during use, and wherein protrusions extend from the surface, said protrusions being configured to extend into the bone to form an engagement with the bone.

4. The eyelet of claim 1 wherein the first end is deformable during use to form an enlarged end that is wider than the cable opening to substantially inhibit the enlarged end from passing into the cable opening, the enlarged end comprising a borehole sized to permit the surgical cable to pass therethrough.

5. The eyelet of claim 1 wherein the first end and the second end are deformable during use to form a first enlarged end and a second enlarged end, respectively, that are wider than the cable opening to substantially inhibit the first and second enlarged ends from passing into the cable opening, the first enlarged end and the second enlarged end comprising a first borehole and a second borehole, respectively, sized to permit the surgical cable to pass therethrough.

6. An eyelet for protecting a bone from a surgical cable, comprising:
    a first substantially elongated eyelet member forming a first bore for housing the surgical cable, the first eyelet member comprising (a) a first portion, (b) a second portion adjoining the first portion and (c) a longitudinal slot, the first bore extending longitudinally through the first portion and the second portion, the first portion comprising a first width such that the first portion is positionable into a cable opening formed in the bone during use, the second portion having a second width greater than a width of the cable opening so as to limit the extent to which the first eyelet member can pass through the cable opening during use; and
    a second substantially elongated eyelet member forming a second bore for housing the surgical cable, the second eyelet member comprising (a) a third portion and (b) a fourth portion adjoining the third portion, the second bore extending longitudinally through the third portion and the fourth portion, the third portion comprising a third width such that the third portion is positionable into the cable opening, the fourth portion having a fourth width greater than the width of the cable opening so as to limit the extent to which the second eyelet member can pass through the cable opening during use;
    and wherein the second eyelet member is substantially aligned with the first eyelet member during use, and wherein the eyelet comprises a biocompatible material, and wherein the eyelet is configured to substantially surround a portion of the surgical cable during use to substantially inhibit the surgical cable portion from contacting the bone.

7. The eyelet of claim 6 wherein the first eyelet member and the second eyelet member are substantially tubular.

8. The eyelet of claim 6 wherein the first eyelet member is configured to form a fixable engagement with the second eyelet member during use.

9. The eyelet of claim 6 wherein the first eyelet member is of substantially the same cross-sectional shape as the second eyelet member.

10. The eyelet of claim 6 wherein the third width is substantially equal to a width of the first bore.

11. The eyelet of claim 6 wherein an inner surface of the first bore comprises at least one groove formed therein and wherein an outer surface of the second eyelet member comprises at least one projection formed thereon for forming a fixable engagement with the at least one groove.

12. The eyelet of claim 6 wherein an inner surface of the first bore comprises a series of substantially parallel grooves formed therein and wherein an outer surface of the second eyelet member comprises a series of substantially parallel projections formed thereon for forming a fixable engagement with the series of grooves.

13. The eyelet of claim 12 wherein the grooves are of substantially uniform size and shape and wherein a depth of each of the grooves increases longitudinally with increasing distance from the second portion, and wherein the projections are of substantially uniform size and shape and wherein a height of each of the projections increases with increasing distance from the fourth portion.

14. The eyelet of claim 6 wherein an inner surface of the first bore comprises a plurality of indentations formed therein and wherein an outer surface of the second eyelet member comprises a plurality of projections formed thereon, the projections being configured to fit within the indentations to secure the first eyelet member to the second eyelet member during use.

15. The eyelet of claim 6 wherein the first eyelet member and the second eyelet member can be snapped together by inserting the second eyelet member into the first eyelet member, and wherein the longitudinal slot allows a width of the first eyelet member to be altered during insertion of the second eyelet member into the first eyelet member.

16. The eyelet of claim 6 wherein the first eyelet member comprises threading and wherein the second eyelet member comprises threading complementary to the threading of the first eyelet member for connecting the first eyelet member to the second eyelet member.

17. The eyelet of claim 6 wherein the first portion comprises an outer surface and wherein the second portion comprises an exterior surface adjacent to and substantially perpendicular to the outer surface of the first portion, the exterior surface comprising protrusions extending therefrom substantially parallel to the outer surface of the first portion, the protrusions being configured to substantially extend into the bone to form an engagement with the bone during use.

18. The eyelet of claim 6 wherein the first portion comprises an outer surface and wherein the second portion comprises an exterior surface adjacent to and substantially perpendicular to the outer surface of the first portion, the exterior surface comprising protrusions extending therefrom substantially parallel to the outer surface of the first portion, the protrusions being configured to substantially extend into the bone to inhibit motion of the eyelet with respect to the bone during use.

19. The eyelet of claim 6 wherein the third portion comprises an outer surface and wherein the fourth portion comprises an exterior surface adjacent to and substantially perpendicular to the outer surface of the third portion, the exterior surface comprising protrusions extending therefrom substantially parallel to the outer surface of the third portion, the protrusions being configured to substantially extend into the bone to form an engagement with the bone during use.

20. The eyelet of claim 6 wherein the third portion comprises an outer surface and wherein the fourth portion comprises an exterior surface adjacent to and substantially perpendicular to the outer surface of the third portion, the exterior surface comprising protrusions extending therefrom substantially parallel to the outer surface of the first portion, the protrusions being configured to substantially extend into the bone to inhibit motion of the eyelet with respect to the bone during use.

21. The eyelet of claim 6 wherein the first portion comprises a first outer surface and wherein the second portion comprises a first exterior surface adjacent to and substantially perpendicular to the first outer surface, the first exterior surface comprising first protrusions extending therefrom substantially parallel to the first outer surface, and wherein the third portion comprises a second outer surface and wherein the fourth portion comprises a second exterior surface adjacent to and substantially perpendicular to the second outer surface, the second exterior surface comprising second protrusions extending therefrom substantially parallel to the second outer surface, the first and second protrusions being configured to substantially extend into the bone to form an engagement with the bone during use.

22. The eyelet of claim 6 wherein the first portion comprises a first outer surface and wherein the second portion comprises a first exterior surface adjacent to and substantially perpendicular to the first outer surface, the first exterior surface comprising first protrusions extending therefrom substantially parallel to the first outer surface, and wherein the third portion comprises a second outer surface and wherein the fourth portion comprises a second exterior surface adjacent to and substantially perpendicular to the second outer surface, the second exterior surface comprising second protrusions extending therefrom substantially parallel to the second outer surface, the first and second protrusions being configured to substantially extend into the bone to inhibit motion of the eyelet with respect to the bone during use.

23. The eyelet of claim 6 wherein the longitudinal slot permits a width of the first eyelet member to be altered during use.

24. The eyelet of claim 6 wherein the biocompatible material comprises a material selected from the group consisting of titanium, stainless steel, plastic, ceramic, polymer, and composite material.

25. A bone protector, comprising:
a first substantially elongated eyelet member means, the first eyelet member means comprising a longitudinal slot, the first eyelet member means forming a first bore, the first eyelet member means comprising (a) a first portion and (b) a second portion adjoining the first portion, the first bore extending longitudinally through the first portion and the second portion, the first portion being positionable within a cable opening formed in a bone during use, the second portion being wider than the cable opening; and
a second substantially elongated eyelet member means, the second eyelet member means forming a second bore, the second eyelet member means comprising (a) a third portion and (b) a fourth portion adjoining the third portion, the second bore extending longitudinally through the third portion and the fourth portion, the third portion being positionable into a cable opening formed in the bone during use, the fourth portion being wider than the cable opening;
and wherein the second eyelet member means is substantially aligned with the first eyelet member means during use, and wherein the first and second bores are configured such that the first and second eyelet member means substantially surround a portion of a surgical cable inserted into the first and second bores during use.

26. A bone protector, comprising:
a first substantially elongated member, said first member configured to be at least partially positionable in a hole formed in a bone, said hole forming a wall;
a bore through the member, said bore configured to prevent surgical cable within the bore from contacting the wall;

a second substantially elongated member, said second member configured to be at least partially positionable in the hole formed in the bone, and said second member configured to couple to the first member;

a bore through the second member, said bore configured to prevent surgical cable within the bore from contacting the wall; and a substantially longitudinal slot in a wall of the second member, said slot extending from an end of the second member that is configured to be coupled to the first member toward a second end of the second member.

27. A method for surgically implanting a cable system comprising:

forming a cable opening in a bone;

inserting an eyelet member in the cable opening, the eyelet member being made of biocompatible material, the eyelet member forming a bore, the eyelet member comprising a first end and a second end opposite the first end; and passing a surgical cable through the bore such that the eyelet member substantially surrounds a portion of the surgical cable so as to substantially inhibit the surgical cable portion from contacting the bone.

28. The bone protector of claim 25, wherein an end of the first elongated eyelet member means is deformable during use to form an enlarged end that is wider than the cable opening to substantially inhibit the enlarged end from passing into the cable opening.

29. The bone protector of claim 25, further comprising protrusions extending from a surface of the first elongated eyelet member means, the protrusions configured to extend into the bone to form an engagement with the bone during use.

30. The bone protector of claim 25, further comprising a threaded end on the first elongated eyelet member means, and a threaded end on the second elongated eyelet member means, wherein the threaded ends are configured to couple together to secure the first elongated eyelet member means to the second elongated eyelet member means during use.

31. The bone protector of claim 26, wherein an end of the first elongated member is deformable during use to form an enlarged end that is wider than the hole in the bone to substantially inhibit the enlarged end from passing into the hole.

32. The bone protector of claim 26, further comprising protrusions extending from a surface of the first elongated member, the protrusions configured to form an engagement with the bone during use.

33. The bone protector of claim 26, further comprising a threaded end on the first elongated member, and a threaded end on the second elongated member, wherein the threaded ends are configured to couple together to secure the first elongated member to the second elongated member during use.

34. The method of claim 27, wherein the cable opening extends substantially through the bone, and wherein the eyelet member extends substantially through the cable opening.

35. The method of claim 27, wherein inserting the eyelet member in the cable opening comprises:

passing the first end of the eyelet member through the cable opening and out of the cable opening; and positioning the eyelet member such that the second end remains outside the cable opening.

36. The method of claim 35, further comprising deforming the first end of the eyelet member to substantially inhibit the first end from passing back into the cable opening.

37. The method of claim 35, further comprising deforming the second end of the eyelet member to substantially inhibit the second end from passing into the cable opening.

38. The method of claim 35, further comprising:

deforming the first end of the eyelet member to substantially inhibit the first end from passing back into the cable opening; and deforming the second end of the eyelet member to substantially inhibit the second end from passing into the cable opening.

39. The method of claim 27, further comprising forming the cable into a loop.

40. The method of claim 39, wherein the cable comprises a first end and a second end and wherein forming the cable into a loop comprises twisting the first end and the second end together.

41. The method of claim 39, wherein the cable comprises a first end and a second end and wherein forming the cable into a loop comprises inserting the first and second ends into a connector.

42. The method of claim 39, wherein the bone is a vertebra and wherein the loop encircles at least one other vertebra.

43. The method of claim 39, wherein the bone is a vertebra and wherein the cable connects the vertebra to a spinal fixation device.

44. The method of claim 39, further comprising tensioning the cable.

45. The method of claim 27 wherein the cable opening is formed substantially at a surface of the bone and wherein the cable opening is at least partially surrounded by the bone.

46. A method for surgically implanting a cable system, comprising:

forming a cable opening in a bone;

inserting an eyelet member in the cable opening, the eyelet member being made of biocompatible material, the eyelet member forming a first bore, the eyelet member comprising a first end and a second end opposite the first end;

forming, at the first end, a fixable engagement between an endpiece and the eyelet member, the endpiece forming a second bore, the endpiece having a width substantially larger than a width of the eyelet member so as to limit an extent to which the engaged endcap and eyelet member can pass through the cable opening; and passing a surgical cable through the second bore and the first bore such that the endpiece and the eyelet member substantially surround a portion of the surgical cable so as to substantially inhibit the surgical cable portion from contacting the bone.

47. A method for surgically implanting a cable system, comprising:

forming a cable opening in a bone;

inserting an eyelet in the cable opening, the eyelet being made of biocompatible material, the eyelet forming a bore, the eyelet comprising (a) a first portion comprising a first end and a second end opposite the first end and (b) a second portion adjoining the first portion at the first end, the bore extending through the first portion and the second portion; and passing a surgical cable through the bore such that the eyelet substantially surrounds a portion of the surgical cable so as to substantially inhibit the surgical cable portion from contacting the bone.

48. A method for surgically implanting a cable system, comprising:

forming a cable opening in a bone;

inserting a first eyelet into the cable opening, the first eyelet being made of biocompatible material, the first eyelet forming a first bore, the first eyelet comprising (a) a first portion comprising a first end and a second end opposite the first end and (b) a second portion adjoining the first portion at the first end, the bore extending through the first portion and the second portion;

inserting a second eyelet into the cable opening, the second eyelet being made of biocompatible material, the second eyelet forming a second bore, the second eyelet comprising (a) a third portion comprising a third end and a fourth end opposite the third end and (b) a fourth portion adjoining the third portion at the third end, the second bore extending through the third portion and the fourth portion; and passing a surgical cable through the first bore and the second bore such that the first eyelet and the second eyelet substantially surround a portion of the surgical cable so as to substantially inhibit the surgical cable portion from contacting the bone.

* * * * *